(12) United States Patent
Kopreski

(10) Patent No.: US 8,030,031 B2
(45) Date of Patent: *Oct. 4, 2011

(54) METHOD ENABLING USE OF EXTRACELLULAR RNA EXTRACTED FROM PLASMA OR SERUM TO DETECT, MONITOR OR EVALUATE CANCER

(75) Inventor: Michael Kopreski, Long Valley, NJ (US)

(73) Assignee: OncoMedx, Inc., Long Valley, NJ (US)

( * ) Notice: Subject to any disclaimer, the term of this patent is extended or adjusted under 35 U.S.C. 154(b) by 236 days.

This patent is subject to a terminal disclaimer.

(21) Appl. No.: 10/912,367

(22) Filed: Jul. 23, 2004

(65) Prior Publication Data

US 2005/0003440 A1 Jan. 6, 2005

Related U.S. Application Data

(63) Continuation of application No. 10/013,294, filed on Dec. 10, 2001, now Pat. No. 6,916,634, which is a continuation of application No. 09/155,152, filed on Sep. 22, 1998, now Pat. No. 6,329,179.

(60) Provisional application No. 60/014,730, filed on Mar. 26, 1996.

(51) Int. Cl.
*C12P 19/34* (2006.01)
*C12Q 1/68* (2006.01)
*G01N 33/00* (2006.01)
*C07H 21/02* (2006.01)
*C07H 21/04* (2006.01)

(52) U.S. Cl. ....... 435/91.2; 435/6; 435/91.1; 435/91.51; 436/94; 536/23.1; 536/24.3; 536/24.33

(58) Field of Classification Search ............. 435/6, 91.1, 435/91.2, 183, 91.51; 436/94; 536/23.1, 536/24.3, 24.33, 25.3
See application file for complete search history.

(56) References Cited

U.S. PATENT DOCUMENTS

| | | |
|---|---|---|
| 4,350,156 A | 9/1982 | Malchesky |
| 4,631,130 A | 12/1986 | Watanabe |
| 4,683,195 A | 7/1987 | Mullis et al. |
| 4,699,877 A | 10/1987 | Cline et al. |
| 4,738,927 A | 4/1988 | Taniguchi |
| 4,874,853 A | 10/1989 | Rossi |
| 4,874,858 A | 10/1989 | Magistro |
| 4,999,290 A | 3/1991 | Lee |
| 5,087,617 A | 2/1992 | Smith |
| 5,098,890 A | 3/1992 | Gerwitz et al. |
| 5,124,246 A | 6/1992 | Urdea et al. |
| 5,155,018 A | 10/1992 | Gillespie et al. |
| 5,217,889 A | 6/1993 | Roninson et al. |
| 5,274,087 A | 12/1993 | Barnett et al. |
| 5,300,635 A | 4/1994 | Macfarlane |
| 5,409,818 A | 4/1995 | Davey et al. |
| 5,429,923 A | 7/1995 | Seidman |
| 5,470,724 A | 11/1995 | Ahern |
| 5,506,106 A | 4/1996 | Croce |
| 5,532,220 A * | 7/1996 | Lee et al. ........................ 514/44 |
| 5,576,178 A | 11/1996 | Emanuel |
| 6,001,987 A | 12/1999 | Perron |
| 6,051,374 A | 4/2000 | Simons |
| 6,057,105 A | 5/2000 | Hoon |
| 6,329,179 B1 | 12/2001 | Kopreski |
| 6,344,317 B2 | 2/2002 | Urnovitz |
| 6,607,898 B1 * | 8/2003 | Kopreski et al. ............. 435/91.2 |
| 6,759,217 B2 * | 7/2004 | Kopreski ..................... 435/91.2 |
| 6,794,135 B1 | 9/2004 | Kopreski |
| 6,916,634 B2 * | 7/2005 | Kopreski ..................... 435/91.2 |
| 6,939,671 B2 * | 9/2005 | Kopreski ......................... 435/6 |
| 2004/0058331 A1 | 3/2004 | Akagi |

FOREIGN PATENT DOCUMENTS

| | | |
|---|---|---|
| DE | 3717212 | 9/2003 |
| WO | WO 90/09456 A1 | 8/1990 |
| WO | WO9009456 A1 | 8/1990 |
| WO | 97/35589 A | 10/1997 |
| WO | 98/14617 A | 4/1998 |
| WO | 99/67397 | 12/1999 |

OTHER PUBLICATIONS

Attached definition for "oncogene" from Web.*
Rykova et al., Concentrations of circulating RNA from healthy donors and cancer patients estimated by different methods. Ann. N.Y. Acad. Sci., 1075, 328-333, 2006.*
Arcari et al., The complete sequence of a full length cDNA for human liver glyceraldehyde-3-phosphate dehydrogenase: evidence for multiple mRNA species. Nucleic Acids Research, 12, 9179-9189, 1984.*
The definitions for "extracellular" and "intracellular" from Wikipedia, the free encyclopedia. Printed on May 15, 2009.*
Tsui et al., Stability of Endogenous and Added RNA in Blood Specimens, Serum, and Plasma. Clin. Chem., 48, 1647-1653, 2002.*
Kopreski et al., "Detection of tumor messenger RNA in the serum of patients with malignant melanoma." Clinical Cancer Research 5:1961-65 (Aug. 1999) 5:1961-65.
Leitzel et a., "Detection of cancer cells in peripheral blood of breast cancer patients using reverse transcription-polymerase chain reaction for epidermal growth factor receptor." Clinical Cancer Research 4:3037-43 (Dec. 1998).

(Continued)

*Primary Examiner* — Frank W Lu
(74) *Attorney, Agent, or Firm* — McDonnell Boehnen Hulbert & Berghoff

(57) ABSTRACT

This invention relates to the use of tumor-derived or associated extracellular ribonucleic acid (RNA) found circulating in the plasma or serum fraction of blood for the detection, monitoring, or evaluation of cancer or premalignant conditions. Specifically, this invention enables the extraction of circulating RNA from plasma or serum and utilizes nucleic acid amplification assays for the identification, detection, inference, monitoring, or evaluation of any neoplasm, benign, premalignant, or malignant, in humans or other animals, which might be associated with that RNA. Further, this invention allows the qualitative or quantitative detection of tumor-derived or associated extracellular RNA circulating in the plasma or serum of humans or animals with or without any prior knowledge of the presence of cancer or premalignant tissue.

7 Claims, No Drawings

OTHER PUBLICATIONS

Tamamiyagi et al., "Quantitative analysis of ferrochelatase mRNA in blood cells of erythropoietic protoprophyria patients." Journal of Dermatological Science 11(2)154-60 (Feb. 1996).

Garbarz et al.,"Spectrin Beta-Tandil A Novel Shortened Beta-Chain Variant Associated with Hereditary Elliptocytosis is due to a Deletional Frameshift Mutation in the Beta Spectrin Gene," Blood 80(4)1066-73 (1992).

Monteyne et al., "Expression of costimulatory molecules and cytokines in CSF and peripheral blood mononuclear cells from multiple sclerosis patients" Acta Neurological Belgica 1(99):11-20 (Mar. 1999).

Serra et al., "Multiple sclerosis and multiple sclerosis-associated retrovirus in Sardinia" Neurological Sciences 22(2) 171-73 (Apr. 2001).

Kopreski et al., "Cellular-versus extracellular-based assays. Comparing utility in DNA and RNA molecular marker assessment" Annals of New York Academy of Sciences 906:124-8 (Apr. 2000).

Messner et al., "Expression of messenger RNA of the cardiac isoforms of troponin T and I in myopathic skeletal muscle" American Journal of Clinical Pathology 114(4)544-49(Oct. 2000).

Kamm et al., "Nucleic-Acid Concentrations in Normal Human Plasma" Clinical Chemistry 18(6)519-22 (1972).

Shutack et al., "A Study of the RNA levels of normal blood serum" The Journal of the American Osteopathic Association 67(9)1051-53 (May 1968).

Guin et al., "Electrophoretic Characterization of Plasma RNA" Biochemical Medicine 13(3)224-30 (1975).

Stroun et al., "Presence of RNA in the nucleoprotein complex spontaneously released by human lymphocytes and frog auricles in culture" Cancer Research 38(10)3546-3554 (Oct. 1978).

Allouche et al., "Expression of basic fibroblast growth factor (bFGF) and FGF-receptors in human leukemic cells" Leukemia:Official Journal of the Leukemia Society of America, Leukemia Reserach Fund 9(1)77-86 (Jan. 1995).

Ricchiuti et al., "Expression of cardiac troponin T mRNA in skeletal muscle from patients with end stage renal disease and muscular dystrophy" Clinical Chemistry 45(6)A144-A145 (Jun. 1999).

Ricchiuti et al., "RNA expression of cardiac troponin T isoforms in diseased human skeletal muscle" Clinical Chemistry 45(12)2129-35 (Dec. 1999).

Ricchiuti et al., "Cardiac troponin I and T alterations in hearts with severe left ventricular remodeling" Clinical Chemistry 43(6)990-95 (1997).

Rosenzweig et al., "Preclinical Diagnosis of Familial Hypertrophic Cardiomyopathy by Genetic Analysis of Blood Lymphocytes" New England Journ of Med 325(25)1753-60 (Nov. 19, 1981).

Spiegelman et al., "The Development and Use of and Extracellular RNA Replicating System" The Harvey Lectures No. 64 pp. 1-67 (1969).

Abravaya et al., "Detection of point mutations with a modified ligase chain reaction (GAP-LCR)," Nucleic Acids Research 23:675-682 (1995).

Alkema et al., "Characterization and Chromosamal Localization of the Human Prata-Oncogene BMI-1," Human Mol Genet 2:1597-1603 (1993).

Aoki et al., "Liposome-mediated in viva gene transfer on antisense K-ras construct inhibits pancreatic tumor dissemination in the murine peritoneal cavity," Cancer Research 55:3810-3816 (1995).

Barz et al., "Characterization of Cellular and Extracellular Plasma Membrane Vesicles from a Non-metastasing Lymphoma (Eb) and Its Metastasing Variant (Esb)," Biochin Biophys Acta 814:77-84 (1985).

Bauer et al., "Identification of H-2Kb Binding and Immunogenic Peptides from Human Papillama Virus Tumour Antigens E6 and E7," Scand J Immunol 42:317-323 (1995).

Blackburn et al., "Electrochemiluminescence detection for development of immunoassays and DNA probe assays for clinical diagnostics," Olin Chem 37/9:1534-1539 (1991).

Bobo et al., "Diagnosis of Chlamydia trachomatis cervical infection by detection of amplified DNA with an enzyme immunoassay," J din Micra 28:1968-1973 (1990).

Bocchia et al., "Specific Binding of Leukemia Oncogene Fusion Peptides to HLA Class I Molecules," Blood 85:2680-2684 (1995).

Boom et al., "Rapid and Simple Method for Purification of Nucleic Acids," J Clin Micro 28:495-503 (1990).

Boom et al., "Rapid Purification of Hepatitis B Virus DNA from Seruc," J Clin Micro 29:180-181 (1991).

Brossart et al., "Detection of residual tumor cells in patients with malignant melanoma responding to immunotherapy," J Immunotherapy 15:38-41 (1994.

Buchman et al., "Selective RNA amplification: A novel method using d UMP-containing primers and uracil DNA glycosylase," PCR Methods Applic 3:28-31 (1993).

Carr et al., "Circulating Membrane Vesicles in Leukemic Blood," Cancer Research 45:5944-5951 (1985).

Cheung et al., "Rapid and Sensitive Method for Detection of Hepatitis C Virus RNA by Using Silica Particles," J Clin Micro 32:2593-2597 (1994).

Chirgwin et al., "Isolation of biologically active ribonucleic acid from sources enriched in ribonuclease," Biochemistry 18:5294-5299 (1979).

Chomczynski and Mackey, "Modification of the TRI reagent (TM) procedure for isolation of RNA from polysaccaride- and proteaglycan-rich sources," Bio Techniques 19:942-945 (1995).

Chomczynski and Mackey, "Substitution of chloroform by bromochloropropane in the single-step method of RNA isolation," Analytical Biochemistry 225:163-164 (1995).

Chomczynski et al., "Single-step method of RNA isolation by acid guanidinium thiocyanate-phenol-chloroform extraction," Analytical Biochemistry 162:156-159 (1987).

Chomczynski, "A reagent for the single-step simultaneous isolation of RNA, DNA and proteins from cell and tissue samples," Biotech 15:532-537 (1993).

Chu et al., "Thymidylate synthase binds to c-myc RNA in human colon cancer cells and in vitro," Mol Cell Biol 15:179-185 (1995).

Cohen, "Biochemical Therapy: Antisense Compounds," In: Biologic Teraphy of Cancer (DeVita, Hellman, Rosenberg, eds) J.B. Lippincott, Ca., Philadelphia (1991) pp. 763-775.

Colomer et al., "erB-2 antisense oligonucleotides inhibit the proliferation of breast carcinoma cells with erb-2 oncogene amplification," Br J Cancer 70:819-825 (1994).

Coutlee et al., "Immunodetection of DNA with biotinylated RNA probes: A study of reactivity of a monoclonal antibody to DNA-RNA hybrids," Analytical Biochemistry 181:96-105 (1989).

Datta et al., "Sensitive Detection of Occult Breast Cancer by the Reverse-transcriptase Polymerase Chain Reaction," Journal of Clinical Oncology 12:475-482 (1994).

Davidova and Shapot, "Liporibonucleoprotein Complex as an Integral Part of Animal Cell Plasma Membranes," FEBS Lett 6:349-351 (1970).

DiCesare et al., "A high-sensitivity electrochemiluminescense-based detection system for automated PCR product quantitation," BioTechniques 15:152-157 (1993).

Doi et al., "Detection of beta-human chorionic ganadotropin mRNA as a marker for cutaneoud malignant melanoma," Int J Cancer 65:454-45-(1996).

Dosaka et al., "A complex pattern of translational initiation and phosphorylation in L-Myc Proteins," Oncogene 6:371-378 (1991).

Edmands et al., "Rapid RT-PCR Amplification from Limited Cell Numbers," PCR Methods Applic 3:317-319 (1994).

Feng et al., "The RNA component of human telomerase," Science 269:1236-1241 (1995).

Fournie et al., "Recovery of nanogram quantities of DNA from plasma and quantitative measurement using labeling by nick translation," Analytical Biochemistry 158:250-256 (1986).

Gerhard et al., "Specific detection of carcinoembryonic antigen-expressing tumor cells in bone marrow aspirates by polymerase chain reaction," J Clin Oncol 12:725-729 (1994).

Ghossein et al., "Detection of Circulating Tumor Cells in Patients with Localized and Metastatic Prostatic Carcinoma: Clinical Implications," Journal of Clinical Oncology 13:1195-1200 (1995).

Higashiyama et al., "Reduced Motility Related Protein-1 (MRP-1/CD9) Gene Expression as a Factor of Poor Prognosis in Non-small Cell Lung Cancer," Cancer Research 55:6040-6044 (1995).

Hoon et al., "Detection of occult melanoma cells in blood with a multiple-marker polymerase chain reaction assay," *J Clin Oncol* 13:2109-2116 (1995).

Hoover et al., "Immunatherapy by Active Specific Immunization: Clinical Applications," *In: Biologic-Therapy of Cancer* (DeVita, Hellman, Rosenberg, eds) J.B. Lippincott, Co., Philadelphia (1991) pp. 670-682.

Imai et al., "Detection of HIV-1 RNA in Heparinized Plasma of HIV-1 Seropositive Individuals," *J Virol Methods* 36:181-184 (1992).

Jrdea et al., "Direct and quantitative detection of HIV-I RNA in human plasma with a branched DNA signal amplification assay," *AIDS* 7(suppl 2):S11-S14 (1993).

Juckett and Rosenberg, "Actions of Cis-diamminedichloroplatinum on Cell Surface Nucleic Acids in Cancer Cells as Determined by Cell Electrophoresis Techniques," *Cancer Research* 42:3565-3573 (1982).

Kahn et al., "Rapid and sensitive nonradioactive detection of mutant K-ras genes via enriched PCR amplification," *Oncogene* 6:1079-1083 (1991).

Kamm and Smith, "Nucleic acid concentrations in normal human plasma," *Clinical Chemistry* 18:519-522 (1972).

Karet et al., "Quantification of mRNA in human tissue using fluorescent nested reverse-transcriptase polymerase chain reaction," *Analytical Biochemistry* 220:384-390 (1994).

Katz et al., "Enhanced Reverse Transcriptase-Polymerase Chain Reaction for Prostate Specific Antigen as a Indicator of True Pathologic Stage in Patients with Prostate Cancer," *Cancer* 75:1642-1648 (1995).

Kievits et al., "NASBA(TM) isothermal enzymatic in vitro nucleic acid amplification optimized for the diagnosis of HIV-1 infection," *J Virological Methods* 35:273-286 (1991).

Kim et al., "Specific association of human telomerase activity with immortal cells and cancer," *Science* 266:2011-2015 (1994).

Komeda et al., "Sensitive detection of circulating heptocellular carcinoma cells in peripheral venous load," *Cancer* 75:2214-2219 (1995).

Landgraf et al., "Direct analysis of polymerase chain reaction products using enzyme-linked immunasorbent assay techniques," *Analytical Biochmistry* 198:86-91 (1991).

Landgraf et al., "Quantitative analysis of polymerase chain reaction (PCR) products using primers labeled with biotin and a fluorescent dye," *Analytical Biochemistry* 193:231-235 (1991).

Larson et al., "Radioisotope Conjugates," *In: Biologic Therapy of Cancer* ( DeVita, Hellman, Rosenberg, eds) J.B. Lippincott, Co., Philadelphia (1991) pp. 496-511.

Leon et al., "A Comparison of DNA and DNA-binding Protein Levels in Malignant Disease," *Europ J Cancer* 17:533-538 (1981).

Maruyama et al., "Detection of AMLi/ETO fusion transcript as a tool for diagnosing t(8;21) positive acute myelogenous leukemia," *Leukemia* 8:40-45 (1994).

Masella et al., "Characterization of Vesicles, Containing an Acylated Oligopeptide, Released by Human Colon Adenocarcinoma Cells," *FEBS Lett* 246:25-29 (1989).

McCabe et al., "Minimal Determinant Expressed by a Recombinant Viaccinia Virus Elicits Therapeutic Antitumor Cytolytic T Lumphocyte Responses," *Cancer Research* 55:1741-1747 (1995).

Miller et al., "Detection of minimal residual disease in acute promyelocytic leukemia by a reverse transcription polymerase chain reaction assay for the PML/RAR-alpha fusion mRNA," *Blood* 82:1689-1694 (1993).

Moore et al., "Design of PCR primers that detect only mRNA in the presence of DNA," *Nucleic Acids Research* 18:1921 (1991).

Mori, et al., "Detection of Cancer Micrometastases in Lymph Nodes by Reverse Transcriptase-Polymerase Chain Reaction," *Cancer Research* 55:3417-3420 (1995).

Mountford et al., "Proteolipid Identified by Magnetic Resonance Spectroscopy in Plasma of a Patient with Borderline Ovarian Tumor," *Lancet* i:829-834 (1987).

Nguyen, "Southern blot analysis of polymerase chain reaction products on acrylamide gels," *BioTechniques* 7:238-240 (1989).

Ozcelik et al., "Low Levels of Expression of an Inhibitor of Cyclin-dependent Kinases (CIP1/WAF1) in Primary Breast Carcinomas with p53 Mutations," *Clinical Cancer Research* 1:907-912 (1995).

Patard et al., "Expression of MAGE genes in transitional-cell carcinomas of the urinary bladder," *mt J Cancer* 64:60-64 (1995).

Penno et al., "Expression of CD44 in human lung tumors," *Cancer Research* 54:1381-1387 (1994).

Peoples et al., "Breast and Ovarian Cancer-Specific Cytotoxic T Lymphocytes Recognize the same HER-2/Neu Derived Peptide," *Proc Natl Acad Sci USA* 92:432-436 (1995).

Pfleiderer et al., "Detection of tumor cells in peripheral blood and bone marrow from ewing tumor patients by RT-PCR," *Int J Cancer (Pred. Oncol)* 64:135-139 (1995).

Polushin et al., "Antisense Pro-Drugs: 5'-ester oligodeoxynucleotides," *Nucleic Acids Research* 22:5492-5496 (1994).

Rashtchian, "Amplification of RNA," *PCR Methods Applic* 4:S83-S91 (1994).

Reddi and Holland, "Elevated Serum Ribonuclease in Patients with Pancreatic Cancer," *Proc Nat Acad Sci USA* 73:2308-2310 (1976).

Rieber and Bacalao, "An 'external' RNA removable from mammalian cells by mild proteolysis," *Proc Natl Acad Sci USA* 71:4960-4964 (1974).

Roggenbuck et al., "Human Papillomavirus Type 18 E6 and E6, and E7 Protein Synthesis in Cell Free Translation Systems and Comparison of E6 and E7 in Vitro Translation Products to Proteins Immunoprecipitated from Human Epthelial Cells," *J Viral* 65:5068-72 (1991).

Rosenberg-Nicolson et al., "Nucleoprotein Complexes Released from Lymphoma Nuclei that Contain the abl Oncogene and RNA and DNA Polymerase and RNA Primase Activities," *J Cell Biochem* 50:43-52 (1992).

Rosi et al., "RNA-Lipid Complexes Released from the Plasma Membrane of Human Colon Carcinoma Cells," *Cancer Lett* 39:153-160 (1988).

Saiki et al., "Genetic analysis of amplified DNA with immobilized sequence-specific oligonucleotide probes," *Science* 233:1076-1078 (1989).

Sakakura et al., "Inhibition of gastric cancer cell proliferation by antisense oligonucleotides targeting the messenger RNA encoding proliferating cell nuclear antigen," *Br J Cancer* 70:1060-1066 (1994).

Schlom, "Antibodies in cancer therapy: basic principles of monaclanal antibodies," *In: Biologic Therapy of Cancer,* (DeVita, Hellman, Hellman, Rosenberg, eds) J.B. Lippincott, Co., Philadelphia (1991) pp. 464-481.

Shea et al., "Identification of the Human Prostate Carcinoma Onogene PTI-1 by Rapid Expression Cloning and Differential RNA Display," *Proc Natl Acad Sci USA* 92:6778-6782 (1995).

Skorski et al., "Suppression of philadelphial leukemia cell growth in mice by BORABL antisense oligodeoxynucleotide," *Proc Natl Acad Sci USA* 91:4504-4508 (1994).

Smith et al., "Detection of Melanoma Cells in Peripheral Blood by Means of Reverse Transcriptase and Polymerase Chain Reaction," *Lancet* 338:1227-1229 (1991).

Sooknanan et al., "Detection and direct sequence identification of BCR-ABL mRNA in Ph+ chronic myeloid leukemia," *Experimental Hematology* 21:1718-1724 (1993).

Stock et al., "Value of molecular monitoring during the treatment of chronic myeloid leukemia: A cancer and leukemia group B study," *J Olin Oncology* 15:26-36 (1997).

Stroun et al., "Neoplastic characteristics of the DNA found in the plasma of cancer patients," *Oncology* 46:318-322 (1989).

Taylor and Blak, "Shedding of Plasma Membrane Fragments. Neoplastic and Developmental Importance," *In: The Cell Surface in Development and Cancer, Develop Biol* 3:33-57 Editor: M.S. Steinberg. Plenum Press, New York, London (1985).

Urdea et al., "Branched DNA amplification multimers for the sensitive, direct detection of human hepatitis viruses," *Nucleic Acids Research Symposium Series* 24:197-200 (1991).

Vandamme et al., "Detection of HIV-1 RNA in plasma and serum samples using the NASBA amplification system compared to RNA-PCR," *J Virological Methods* 52:121-132 (1995).

Vitetta et al., "Immunatoxins," *In: Biologic Therapy of Cancer* (DeVita, Hellman, Rosenberg, eds) J.B. Lippincott, Co., Philadelphia (1991) pp. 482-495.

Wang et al., "Quantitation of mRNA by the polymerase chain reaction," *Proc Natl Acad Sci USA* 86:9717-9721 (1989).
Wieczorek et al., "Diagnostic and Prognostic Value of RNA-Proteolipid in Sera of Patients with Malignant Disorders Following Therapy; First Clinical Evaluation of a Novel Tumor Marker," *Cancer Research* 47:6407-6412 (1987).
Wieczorek et al., "Gensondentest Fur RNA-Proteolipid in Serumproben Bei Neoplasie," *Schweiz med Wschr* 119:1342-1343 (1989).
Wieczorek et al., "Isolation and Characterization of art RNA-Proteolipid Complex Associated with the Malignant State in Humans," *Proc Natl Acad Sci USA* 82:3455-3459 (1985).
Wiedmann et al., "Ligase chain reaction (LCR)—overview and applications," *POR Methods Applic* 3:551-564 (1994).
Yanuck et al., "A Mutant P53 Tumor Suppressor Protein is a Target f or Peptide-Induced 0DB' Cytotoxic T-Cells," *Cancer Research* 52:3257-3261 (1993).
Zhou et al., "Circulating RNA as a novel tumor marker: An in vitro study of the origins and characteristics of extracellular RNA". Cancer Letter 259:50-60 (2008).
Office Action, Non-Final Rejection mailed on Nov. 4, 1999 for U.S. Appl. No. 09/155,152.
Office Action, Non-Final Rejection mailed on Apr. 20, 2000 for U.S. Appl. No. 09/155,152.
Office Action, Final Rejection mailed on Oct. 25, 2000 for U.S. Appl. No. 09/155,152.
Office Action, Final Rejection mailed on Apr. 20, 2001 for U.S. Appl. No. 09/155,152.
Office Action, Non-Final Rejection mailed on Nov. 4, 1999 for U.S. Appl. No. 09/210,671.
Office Action, Non-Final Rejection mailed on Aug. 7, 2002 for U.S. Appl. No. 09/966,515.
Office Action, Non-Final Rejection mailed on Nov. 19, 2002 for U.S. Appl. No. 09/966,515.
Office Action, Non-Final Rejection mailed on Dec. 4, 2002 for U.S. Appl. No. 10/013,868.
Office Action, Final Rejection mailed on May 20, 2003 for U.S. Appl. No. 10/013,868.
Office Action, Non-Final Rejection mailed on Oct. 25, 2002 for U.S. Appl. No. 10/013,294.
Office Action, Non-Final Rejection mailed on Aug. 30, 2005 for U.S. Appl. No. 10/201,382.
Office Action, Final Rejection mailed on Mar. 15, 2006 for U.S. Appl. No. 10/201,382.
Office Action, Non-Final Rejection mailed on Jan. 10, 2007 for U.S. Appl. No. 10/201,382.
Office Action, Final Rejection mailed on Sep. 10, 2007 for U.S. Appl. No. 10/201,382.
Office Action, Non-Final Rejection mailed on Nov. 16, 2005 for U.S. Appl. No. 10/288,935.
Office Action, Final Rejection mailed on Jun. 12, 2006 for U.S. Appl. No. 10/288,935.
Office Action, Non-Final Rejection mailed on Feb. 23, 2007 for U.S. Appl. No. 10/288,935.
Office Action, Final Rejection mailed on Oct. 4, 2007 for U.S. Appl. No. 10/288,935.
Office Action, Non-Final Rejection mailed on Aug. 24, 2006 for U.S. Appl. No. 10/658,873.
Office Action, Final Rejection mailed on Apr. 9, 2007 for U.S. Appl. No. 10/658,873.
Office Action, Non-Final Rejection mailed on Jan. 28, 2008 for U.S. Appl. No. 10/658,873.
Office Action, Final Rejection mailed on Jul. 10, 2008 for U.S. Appl. No. 10/658,873.
Office Action, Non-Final Rejection mailed on Dec. 15, 2006 for U.S. Appl. No. 10/684,633.
Office Action, Final Rejection mailed on Jun. 21, 2007 for U.S. Appl. No. 10/684,633.
Office Action, Non-Final Rejection mailed on Jan. 28, 2008 for U.S. Appl. No. 10/684,633.
Office Action, Non-Final Rejection mailed on May 3, 2007 for U.S. Appl. No. 10/912,367.
Office Action, Final Rejection mailed on Aug. 10, 2007 for U.S. Appl. No. 10/912,367.
Office Action, Non-Final Rejection mailed on Feb. 6, 2008 for U.S. Appl. No. 10/912,367.
Office Action, Final Rejection mailed on Dec. 1, 2008 for U.S. Appl. No. 10/912,367.
Office Action, Non-Final Rejection mailed on Apr. 2, 2008 for U.S. Appl. No. 11/216,858.
Office Action, Final Rejection mailed on Nov. 14, 2008 for U.S. Appl. No. 11/216,858.
Office Action, Non-Final Rejection mailed on Oct. 2, 2008 for U.S. Appl. No. 11/346,590.
Office Action, Non-Final Rejection mailed on Nov. 13, 2008 for U.S. Appl. No. 11/357,399.
Office Action, Non-Final Rejection mailed on Sep. 22, 2008 for U.S. Appl. No. 11/364,842.
Office Action, Non-Final Rejection mailed on Sep. 10, 2008 for U.S. Appl. No. 11/421,260.
Office Action, Non-Final Rejection mailed on Jan. 8, 2009 for U.S. Appl. No. 11/416,470.
Office Action, Non-Final Rejection mailed on Oct. 8, 2008 for U.S. Appl. No. 11/416,788.
Rajagopal et al. (1995), Int. J. Cancer 62: 661-667.
Dahiya et al. (1996), Urology 48: 963-970.
LeRiche et al. (1996), J. Clin. Endocrinol. Metab. 81: 656-662.
Pfeiffer et al. (1997), Int. J. Cancer 72: 581-586.
De Luca et al. (2000), Clin. Cancer Res. 6: 1439-1444.
Schlegel et al. (1994), Int. J. Cancer 56: 72-77.
Worm et al. (1999), Hum. Pathol. 30: 222-227.
Pawlowski et al. (2000), Cancer Detect. Prev. 24: 212-223.
Walch et al. (2001), Lab. Invest. 81: 791-801.
Sarkar et al. (1993), Diagn. Mol. Pathol. 2: 210-218.
Gebhardt et al. (1998), Biochem. Biophys. Res. Comm. 247: 319-323.
Revillion et al. (1997), Clin. Chem. 43: 2114-2120.
Schneeberger et al. (1996), Anticancer Res. 16: 849-852.
Kraehn et al. (2001), Br. J. Cancer 84: 72-79.
Gamberi et al. (1998), Oncology 55: 556-563.
Sagawa et al. (2001), Cancer Letters 168: 45-50.
Christoph et al. (1999). Int. J. Cancer 84: 169-173.
Latil et al. (2000), Int. J. Cancer 89: 172-176.
Zhou et al. (1996), J. Biol. Chem. 271: 10760-10766.
Kozu et al. (1995), Genomics 25: 365-371.
Gocke et al. (2001), Clin. Chem. 47: 369, abstract 51.
Poon et al. (2001), Clin. Chem. 47: 363, abstract 11.
Urnovitz et al. (1999), Clin. Diag. Lab. Immunology 6: 330-335.
Zhao et al. (1994), Circulation 90: 677-685.
Dhillon et al. (2001), Exp. Neurol. 170: 140-148.
Fleischhacker et al. (2001), Clin. Chem. 47: 369 (Oral Presentation).
El-Hefnawy et al. (2004), Clin. Chem. 50(3): 564-573.
Tschentscher et al. (2000), Int. J. Clin. Lab. Res. 30(1): 13-15.
Missov et al. (1999), Clinica Chimica Acta 284: 175-185.
Sarko et al. (2002), J. Emerg. Med. 23(1): 57-65.
Jurlander et al. (2000), Eur. Heart J. 21: 382-389.
Rainer et al. (2004), Clin. Chem. 50(1): 206-208.
Townsend et al. (1995), J. Mol. Cell. Cardiol. 27: 2223-2236.
Mizuno et al. (2001), Blood 97(5): 1172-1179.
Meikl et al. (1998), Leukemia 12: 311-316.
Lee et al. (1996), Proc. Natl. Acad. Sci. U. S. A. 93: 10366-10370.
Eads et al. (1999), Cancer Res. 59: 2302-2306.
Robertson et al. (1999), Nucleic Acids Res. 27(11): 2291-2298.
Fleischhacker and Schmidt (2007), Biochim. Biophys. Acta 1775: 181-232.
Lion et al. (1995), Leukemia 9: 1353-1360.
El-Deiry, et al. (1991), Proc. Natl. Acad. Sci. U. S. A. 88: 3470-3474.
Lo et al. (1999), Clin. Chem. 45(8): 1292-1294.
Chen et al. (1999), Int. J. Cancer 83: 10-14.
Saito et al. (2001), Hepatology 33: 561-568.
Serra et al. (2001), Neurological Sciences 22(2): 171-173.
Shen et al. (1995), Proc. Natl. Acad. Sci. U. S. A. 92: 6778-6782.
Shutack et al. (1968), J. Am. Osteopath. Assoc. 67(9): 1051-1053.
Spiegelman et al. (1969), The Harvey Lectures No. 64, pp. 1-67.
Stroun et al. (1978), Cancer Res. 38(10): 3546-3554.

Tamamiyagi et al. (1996), J. Dermatol. Sci. 11(2): 154-60.
Urdea et al. (1993), AIDS 7(suppl. 2): S11-S14.
Rohde et al. (2000), Clin. Cancer Res. 6: 4803-4809.
Keller et al. (1993), PCR Methods and Applications 3: 32-38.
Nolte et al. (1994), J. Clin. Microbiology 32: 519-520.
Schmidt et al. (1995), J. Med. Virology 47: 153-160.
Agliullina et al. (1988), Eksp. Onkol (USSR) 10(4), English abstract, only.
Schwarz et al. (1995), Res. Virol (Paris) 146(5), English abstract, pp. 355-362.
Kato et al. (1993), Hepatology 18(1), abstract.
Glick et al. (1994), Molecular biotechnology: Principles and applications of recombinant DNA, ASM Press: Washington DC. Table of Contents for Molecular Diagnostics (8) and Vaccines and Therapeutic Agents (9), only.
Persing et al (1993), Diagnostic molecular microbiology: Principles and applications, Amer. Soc. Microbiol. Washington DC, Table of Contents for Principles of Diagnostic Molecular Microbiology and Viral Pathogens, only.
Southall et al. (1990), Br. J. Cancer 61: 89-95.
Kopreski et al. (2001), Ann. N.Y. Acad. Sci 945: 172-178.
Yan-Sanders et al. (2002), Cancer Letters 183: 215-220.
Khimani et al. (2005), BioTechniques 38: 739-745.
Schrader et al. (2002), BMC Cancer 2: 32.
Fleischhacker et al. (2001), Ann. N.Y. Acad. Sci. 945: 179-188.
Burd et al. (1989), Proc. Natl. Acad. Sci. U.S.A. 86: 9788-9792.
Burchill et al. (1995), Br. J. Cancer 71: 278-281.
Lasheeb et al. (1997), Genitourinary Medicine 73(4): 303-305.
Mermin et al. (1991), J. Infectious Diseases 164(4): 769-772.
Kopreski et al. (2001), Clin. Chem. 47: 362, abstract 9.
Pelosi et al. (2006), Virchows Arch. 448: 7-15.
Tahara et al. (1999), Oncogene 18: 1561-1567.
Dasi et al. (2001), Lab. Investigation 81: 767-769.
Hasselmann et al. (2001), Oncol. Rep. 8: 115-118.
Ng et al. (2002), Clin. Chem. 48: 1212-1217.
Chen et al. (2000), Clin. Cancer Res. 6: 3823-3826.
Silva et al. (2001), Clin. Cancer Res. 7: 2821-2825.
Silva et al. (2001), Oncol. Rep. 8: 693-696.
Gal et al. (2001), Ann. N.Y. Acad. Sci. 945: 192-194.
Durie et al. (2000), Acta Oncol. 39: 789-796.
Miura et al. (2003), Oncology 64: 430-434.
Wong et al. (2004), J. Clin. Pathol. 57: 766-768.
Ma et al. (2007), Haematologica 92: 170-175.
Arcari et al. (1984), Nucleic Acids Res. 12: 9179-9189.
Rykova et al. (2006), Ann. N.Y. Acad. Sci. 1075: 328-333.
Hernandez et al. (1999), Leukemia 13: 2087-2093.
Zhou et al. (1998), Clin. Cancer Res. 4: 1631-1640.
Zhou et al. (2001), Breast Cancer Research and Treatment 66: 217-224.
Press et al. (1990), Oncogene 5: 953-962.
Ng et al. (2003), Proc. Natl. Acad. Sci. U.S.A. 100: 4748-4753.
Gilmour et al. (2001), Cancer Res. 61: 2169-2716.
Reinhold et al. (2001), Clin. Chem. 47: 369, abstract 50.
Bairey et al., (2002), Arch. Pathol. Lab Med. 126:574-76.
Kanbara et al., "Clinical significance of serum AFP-mRNA in the hepatocellular carcinoma (HCC) patient," International hepatology Communications Jul. 1995. Abstract.
Moreno et al. (1992), Cancer Res. 52: 6110-6112.

* cited by examiner

SEQUENCE LISTING

<160> NUMBER OF SEQ ID NOS: 8

<210> SEQ ID NO 1
<211> LENGTH: 26

```
<212> TYPE: DNA
<213> ORGANISM: Homo sapiens

<400> SEQUENCE: 1
tggagctgca gatgctgacc aactgg                                          26

<210> SEQ ID NO 2
<211> LENGTH: 26
<212> TYPE: DNA
<213> ORGANISM: Homo sapiens

<400> SEQUENCE: 2
atctccactg gccacaaaat cataca                                          26

<210> SEQ ID NO 3
<211> LENGTH: 22
<212> TYPE: DNA
<213> ORGANISM: Homo sapiens

<400> SEQUENCE: 3
gaagtgtttc agaagcttct cc                                              22

<210> SEQ ID NO 4
<211> LENGTH: 22
<212> TYPE: DNA
<213> ORGANISM: Homo sapiens

<400> SEQUENCE: 4
tgattatagc ctaagacccg ga                                              22

<210> SEQ ID NO 5
<211> LENGTH: 20
<212> TYPE: DNA
<213> ORGANISM: Homo sapiens

<400> SEQUENCE: 5
ttggcagatt gtctgtagcc                                                 20

<210> SEQ ID NO 6
<211> LENGTH: 20
<212> TYPE: DNA
<213> ORGANISM: Homo sapiens

<400> SEQUENCE: 6
aggcattgtg catgctgctt                                                 20

<210> SEQ ID NO 7
<211> LENGTH: 20
<212> TYPE: DNA
<213> ORGANISM: Homo sapiens

<400> SEQUENCE: 7
gtctttatgc aatggaacgc                                                 20

<210> SEQ ID NO 8
<211> LENGTH: 20
<212> TYPE: DNA
<213> ORGANISM: Homo sapiens

<400> SEQUENCE: 8
gctatcccag taagtggact                                                 20
```

METHOD ENABLING USE OF EXTRACELLULAR RNA EXTRACTED FROM PLASMA OR SERUM TO DETECT, MONITOR OR EVALUATE CANCER

This application is a continuation of U.S. Ser. No. 10/013,294, filed Dec. 10, 2001, now U.S. Pat. No. 6,916,634, which is a continuation of U.S. Ser. No. 09/155,152, filed Sep. 22, 1998, now U.S. Pat. No. 6,329,179, which application claims the benefit of the filing date of U.S. Provisional Application Ser. No. 60/014,730, filed Mar. 26, 1996, the entire disclosures of U.S. Ser. No. 09/155,152 and Ser. No. 60/014,730 are explicitly incorporated by reference herein.

BACKGROUND OF THE INVENTION

Ribonucleic acid (RNA) is essential to the processes which allow translation of the genetic code to form proteins necessary for all cellular functions, both in normal and neoplastic cells. While the genetic code structurally exists as deoxyribonucleic acid (DNA), it is the function of RNA, existing as the subtypes transfer-RNA, messenger-RNA or messenger-like RNA, and ribosomal-RNA, to carry and translate this code to the cellular sites of protein production. In the nucleus, this RNA may further exist an or in association with ribonucleoproteins (RNP). The pathogenesis and regulation of cancer is dependent upon RNA-mediated translation of specific genetic codes, which often reflects mutational events within oncogenes, to produce proteins involved with cell proliferation, regulation, and death. Furthermore, other RNA and their translated proteins, although not necessarily those involved in neoplastic pathogenesis or regulation, may serve to delineate recognizable characteristics of particular neoplasms by either being elevated or inappropriately expressed. Thus, recognition of specific RNA can enable the identification, detection, inference, monitoring, or evaluation of any neoplasm, benign, malignant, or premalignant, in humans and animals. Furthermore, since RNA can be repetitively created from its DNA template, for a given gene within a cell there may be formed a substantially greater number of associated RNA molecules than DNA molecules. Thus, an RNA-based assay should have greater sensitivity, and greater clinical utility, than its respective DNA-based assay. Note that the term RNA denotes ribonucleic acid including fragments of ribonucleic acid consisting of ribonucleic acid sequences.

RNA based nucleic acid amplification assays, including the reverse transcriptase polymerase chain reaction (RT-PCR, also known as reverse transcription polymerase chain reaction or RNA-PCR), branched DNA signal amplification, and self-sustained sequence replication assays, such an isothermal nucleic acid sequence based amplification (NASBA), have proven to be highly sensitive and specific methods for detecting small numbers of RNA molecules. As such, they can be used in direct assays of neoplastic tissue (1-3). Since peripheral blood is readily obtainable from patients with cancer, and metastatic cancer cells are known to circulate in the blood of patients with advanced cancer, several investigators have recently used RT-PCR to detect intracellular RNA extracted from circulating cancer cells (4-7). It must be emphasized that currently investigators apply RT-PCR to detect extracted intracellular RNA from a predominately cellular fraction of blood in order to demonstrate the existence of circulating cancer cells. RT-PCR is applied only to the cellular fraction of blood obtained from cancer patients, i.e., the cell pellet or cells within whole blood. The plasma or serum fraction of blood is usually discarded prior to analysis, but is not examined separately. Since such a cellular fraction approach relies upon the presence of metastatic circulating cancer cells, it is of limited clinical use in patients with early cancers, and is not useful in the detection of non-invasive neoplasms or pre-malignant states.

The invention described by this patent application demonstrates the novel use of that human or animal tumor-derived or tumor-associated RNA found circulating in the plasma or serum fraction of blood, as a means to detect, monitor, or evaluate cancer and premalignant states. This invention is based upon the application of RNA extraction techniques and nucleic acid amplification assays to detect tumor-derived or associated extracellular RNA found circulating in plasma or serum. In contrast to the detection of viral-related RNA in plasma or serum, and the detection of tumor-associated DNA in plasma and serum, the detection of human or mammalian RNA, and particularly tumor-derived or associated RNA, has never been detected specifically within the plasma or serum fraction of blood using nucleic acid amplification methodology, and thus represents a novel and non-obvious use for these RNA extraction methods and nucleic acid amplification assays. Since this invention is not dependent upon the presence of circulating cancer cells, it is clinically applicable to cases of early cancer, non-invasive cancers, and premalignant states, in addition to cases of invasive cancer and advanced cancer. Further, this invention allows the detection of RNA in previously frozen or otherwise stored plasma and serum, thus making plasma and serum banks available for analysis and otherwise increasing general usefulness.

Tumor-derived or tumor-associated RNA that in present in plasma and serum may exist in two forms. The first being extracellular RNA, but the second being extractable intracellular RNA from cells occasionally contaminating the plasma or serum fraction. In practice, it in not necessary to differentiate between intracellular and extracellular in order to detect RNA in plasma or serum using the invention, and this invention can be used for detection of both. The potential uses of tumor-derived or associated extracellular RNA have not been obvious to the scientific community, nor has the application of nucleic acid amplification assays to detect tumor-derived or associated extracellular RNA been obvious. Indeed, the very existence of tumor-derived or associated extracellular RNA has not been obvious to the scientific community, and is generally considered not to exist. It is generally believed that plasma ribonucleases rapidly degrade any extracellular mammalian RNA which might circulate in blood, rendering it nondetectable (8). Kameda et al., for example, specifically added free RNA to whole blood obtained from normal volunteers, but were unable to detect that RNA using PCR (54). However, nucleases appear inhibited in the plasma of cancer patients (9). In addition, extracellular RNA, either complexed to lipids and proteolipids, protein-bound, or within apoptotic bodies, would be protected from ribonucleases. Thus, although still undefined, tumor-derived or associated extracellular RNA may be present in plasma or serum via several mechanisms. Extracellular RNA could be secreted or shed from tumor in the form of lipoprotein (proteo-lipid)-RNA or lipid-RNA complexes, it could be found within circulating apoptotic bodies derived from apoptotic tumor cells, it could be found in proteo-RNA complexes released from viable or dying cells including or in association with ribonucleoproteins, or in association with other proteins such as galectin-3, or RNA could be released from necrotic cells and then circulate bound to proteins normally present in plasma. Additionally it could exist circulating within RNA-DNA complexes including those associated with ribonucleoproteins and other nucleic RNA. Further, RNA may exist within several of these moieties simultaneously. For example, RNA may be found associated with ribonucleoprotein found within proteo-lipid apoptotic bodies. The presence of extracellular RNA in plasma or serum makes their detection by nucleic acid amplification assays feasible.

Several studies in the literature support the existence of tumor-derived or associated extracellular RNA. RNA has been shown to be present on the cell surface of tumor cells, as demonstrated by electrophoresis (10), membrane preparations (11), and $p^{32}$ release (12). Shedding of phospholipid vesicles from tumor cells is a well described phenomena (13, 14), and similar vesicles have been shown to circulate in the blood of patients with cancer (15). Kamm and Smith used a fluorometric method to quantitate RNA concentrations in the plasma of healthy individuals (55). Rosi and colleagues used high resolution nuclear magnetic resonance (NMR) spectroscopy to demonstrate RNA molecules complexed with lipid vesicles which were shed from a human colon adenocarcinoma cell line (16). Further characterization of these lipid-RNA complexes demonstrated the vesicles additionally contained triglyceride, cholesterol esters, lipids, oligopeptide, and phospholipids (17). Mountford et al. used magnetic resonance spectroscopy to identify a proteolipid in the plasma of a patient with an ovarian neoplasm (18). While further evaluation of the proteolipid using the orcinol method suggested RNA was present, this could not be confirmed using other methods. Wieczorek and associates, using UV spectrometry and hydrolysis by RNases, claimed to have found a specific RNA-proteolipid complex in the serum of cancer patients which was not present in healthy individuals (19-20). The complex had unvarying composition regardless of the type cancer. Wieczorek et al. were further able to detect this specific RNA-proteolipid complex using a phage DNA cloned into. E. coli and hybridized to RNA from neoplastic serum, a method distinctly different from the method of this invention. The DNA was then detected by immunoassay (21). However, the RNA found in this complex is described as 10 kilobases, which is so large as to make it questionable whether this truly represents RNA as described. More recently, DNA and RNA-containing nucleoprotein complexes, possibly representing functional nuclear suborganellular elements, were isolated from the nuclei of lymphoma cells (22). It was not shown, however, that these complexes can be shed extracellularly. Other ribonucleoprotein complexes have been associated with c-myc oncogene RNA (56).

While plasma and serum are generally presumed to be cell-free, in the practical sense, particularly under conditions of routine clinical fractionation, plasma and serum may occasionally be contaminated by cells. These contaminating cells are a source of intracellular RNA which is detectable by the methods of the invention. While the level of contaminating cells may be reduced by filters or high speed centrifugation, these methods may also reduce extracellular RNA, particularly larger apoptotic bodies. Clinical utility of the invention is not dependent upon further separating of plasma or serum RNA into its extracellular and intracellular species. Similar analogy likely exists for detection of normal RNA (non-tumor derived or non-tumor associated RNA) in plasma and serum. Subsequent to the filing of the provisional patent application for this patent, the inventor has shown that normal RNA (non-tumor derived RNA) could similarly be detected in the plasma or serum of both healthy volunteers and cancer patients using extraction methods and amplification methods as described by this invention. Qualitative results suggested that amplified product was greater when obtained from cancer patients. Further, use of a 0.5 micron filter prior to amplification reduced, but did not eliminate amplifiable RNA, consistent with extracellular RNA being of variable size, with additional contaminating cells possible.

While the methods of RNA extraction utilized in this invention have been previously used to extract both viral RNA and intracellular RNA, their applicability to extracellular tumor-related or tumor-associated RNA was not obvious. The physical characteristics of the extracellular RNA complexes remain largely unknown, and thus it was not known prior to this invention if the methods of extraction to be described could effectively remove extracellular RNA from their proteolipid, apoptotic, vesicular, or protein-bound complexes. This invention describes the applicability of these RNA extraction methods to the extraction of extracellular RNA from plasma or serum, and thus describes a new use for these extraction methods.

In summary, this invention describes a method by which RNA in plasma or serum can be detected and thus utilized for the detection, monitoring, or evaluation of cancer or premalignant conditions. This method utilizes nucleic acid amplification assays to detect human or animal tumor-derived or associated extracellular RNA circulating in plasma or serum. It also enables extraction and amplification of intracellular RNA should cells be present in plasma or serum. The described extraction methods and various nucleic acid amplification assays, including but not limited to RT-PCR, branched DNA signal amplification, transcription-based amplification, amplifiable RNA reporters, boomerang DNA amplification, strand displacement activation, cycling probe technology, isothermal NASBA amplification, and other self-sustained sequence replication assays, have not been used for the detection of tumor-derived or tumor-associated RNA in plasma or serum, reflecting the general scientific bias that mammalian extracellular RNA does not exist circulating in plasma or serum, despite isolated studies to the contrary. Thus, this invention represents both a novel and non-obvious method of detecting, monitoring, and evaluating cancer or premalignant conditions, and a novel and non-obvious application of both RNA extraction methodology and nucleic acid amplification assays. This invention, as described below entails a multi-step procedure applied to plasma or serum which consists of three parts with the initial step (Part A) involving extraction of tumor-derived or associated RNA from plasma or serum, a second step (Part B) involving application of a nucleic acid amplification assay, in which reverse transcription of RNA to its cDNA may be involved, and a third step (Part C) involving detection of the amplified product. Any nucleic acid amplification assay capable of permitting detection of small numbers of RNA molecules or their corresponding cDNA may be used in Part B. Similarly, various methods of detection of amplified product may be used in Part C, including but not limited to agarose gel electrophoresis, ELISA detection methods, electrochemiluminescence, high performance liquid chromatography, and reverse dot blot methods. Furthermore, Part B and Part C may utilize assays which enable either qualitative or quantitative RNA analysis. Thus, while this invention uses various methods described in the literature, it is the unique application of these methods to the detection of tumor-derived or associated extracellular RNA from plasma or serum that makes this invention novel. This invention provides a simple means for testing blood plasma or serum for tumor-derived or associated RNA, with the result of identifying patients harboring tumor cells. Since this invention enables detection of extracellular RNA, and does not depend upon the presence of circulating cancer cells, it offers a sensitive yet inexpensive screen for both malignancy and pre-malignancy, as well as a way for monitoring cancer and obtaining other prognostically important clinical information.

OBJECTS AND APPLICATIONS OF THE INVENTION

It is therefore the object of this invention to detect or infer the presence of cancerous or precancerous cells whether from non-hematologic or hematologic malignancy, within a human or animal body, both in those known to have cancer and in those not previously diagnosed, by examining the plasma or serum fraction of blood for tumor-derived or associated extracellular RNA, including, but not limited to, that derived from mutated oncogenes, using nucleic acid amplification assays, such as, but not limited- to, polymerase chain reaction (RT-PCR), branched DNA signal amplification, isothermal nucleic acid sequence based amplification (NASBA), other self-sustained sequence replication assays, transcription-based amplification, boomerang DNA amplification, strand displacement activation, cycling probe technology, and amplifiable RNA reporters.

An application of this invention is to allow identification or analysis, either quantitatively or qualitatively, of tumor-derived or associated RNA in the blood plasma or serum of humans or animals during or following surgical procedures to remove premalignant or malignant lesions, and thus to allow stratification of such patients as to their risk of residual cancer following the surgery.

Another application of this invention is to allow identification or analysis, either quantitatively or qualitatively, of tumor-derived or associated RNA in the blood plasma or serum of humans or animals who are receiving cancer therapies, including but not limited to biotherapy, chemotherapy, or radiotherapy, as a guide to whether adequate therapeutic effect has been obtained or whether additional or alternative therapy is required, and further, to assess prognosis in these patients.

Another application of this invention is to allow identification or analysis, either quantitatively or qualitatively, of tumor-derived or associated RNA in the blood plasma or serum of humans or animals who have completed therapy as an early indicator of relapsed cancer, impending relapse, or treatment failure.

Another application of this invention is to allow identification, either by detection or by inference, of the presence of premalignant neoplasm including dysplasias or adenomas by the examination of blood plasma or serum for RNA derived from or associated with those neoplasms. Furthermore, analysis, for example by a panel of assays to detect various RNA, may serve to distinguish malignant from premalignant conditions, or assist in medical monitoring to detect transformation of a neoplasm to an outright malignancy, or to detect regression.

Thus, an application of this invention is to provide a method of screening both individuals without known risk, and individuals at risk, for cancer and premalignant conditions, and further, for defining risk of cancer when that risk is unknown.

Another application of this invention in to allow identification or analysis, either quantitatively or qualitatively, of tumor-derived or associated RNA in the blood plasma or serum of humans or animals either newly or recently diagnosed with cancer or a premalignant condition in order to clarify when to initiate therapy, including adjuvant therapies.

Another application of this invention is to allow identification or analysis of tumor-derived or associated MA, either singularly or by a panel approach detecting varied RNA, in the blood plasma or serum of humans or animals in order to determine specific characteristics of a given patients tumor, as to assist in the development of patient-specific therapies, help direct a given patient into a given treatment regimen, or help predict prognosis or tumor behavior.

SUMMARY OF THE INVENTION

The objects, advantages and applications of the present invention are achieved by the hereinafter described method for detecting tumor derived or associated extracellular RNA from body fluids, in particular from mammalian blood plasma or serum by (A) extraction of RNA from blood plasma or serum; (B) amplification of the RNA by nucleic acid amplification assays, including (11 reverse transcription polymerase chain reaction (RT-PCR), ligase chain reaction, branched DNA signal amplification, transcription-based amplification, amplifiable RNA reporters, Q-beta replication, boomerang DNA amplification, strand displacement activation, cycling probe technology, isothermal nucleic acid sequence based amplification (NASBA) and self-sustained sequence replication assays. The primers used may be selected for their ability to characterize the tumor; and (C) detection of the specific amplified RNA.

This method of detection can be employed in various methods of use including the detection of early cancers and premalignant neoplasms and invasive or advanced cancers, and for the monitoring of patients during treatment therapy and for post-operative monitoring, and to develop appropriate patient-specific treatment strategies as described herein.

DETAILED DESCRIPTION OF THE INVENTION

The use of RNA detection is preferred in many circumstances over DNA detection since a greater number of RNA molecules are potentially available, thus allowing potentially greater sensitivity. Furthermore, since wild-type DNA genetic information is identical in all somatic cells of an individual, discrimination between normal and tumor-associated DNA is dependent upon the presence of a mutation. Detection of RNA, by reflecting activity of the gene, allows demonstration of an inappropriately expressing non-mutated gene, as in typically seen in malignancy. Thus, RNA amplification methods allow a way to detect gene expression, whether normal or mutated, which is turned on in cancer. The present invention provides a much greater applicability and versatility to monitoring cancer than do any methods based on DNA analysis. For a DNA method to detect cancers from normal, there must be some mutation or genetic rearrangement present in the cancer, but not in the normal. The present process of using RNA will similarly detect the mutant RNA produced from this DNA. However, it further allows detection of inappropriately expressing "normal" genes. Thus, compared to methods detecting DNA, methods detecting RNA provide greater versatility and applicability in addition to the expected greater sensitivity.

This invention relates to a method of detecting or inferring the presence of cancerous or precancerous cells, whether from a non-hematologic malignancy (i.e., solid tumor) or from a hematologic malignancy, in a human or animal by the combination of three steps applied to plasma or serum. The first step (Part A) involves the extraction of tumor-derived or associated RNA from blood plasma or serum. The second step (Part B) applies a nucleic acid amplification assay to the extracted RNA. In this step, the extracted RNA may first be reverse transcribed to cDNA prior to amplification of the cDNA. The third step (Part C) allows for the detection of the amplified product. Parts B and C may be performed as to allow either qualitative or quantitative detection of the RNA, depending upon the ultimate clinical objective or application, as described herein. Various methods, as detailed below, may be used in Part A similarly, any nucleic acid amplification assay which can be utilized in the detection of small numbers of RNA or corresponding cDNA molecules, including but not limited to the polymerase chain reaction (RT-PCR), branched DNA signal amplification, ligase chain reaction, isothermal nucleic acid sequence based amplification (NASBA), Q-beta replication, transcription-based amplification, amplifiable RNA reporters, boomerang DNA amplification, strand displacement activation, cycling probe technology, and other self-sustained sequence replication assays, as well as variations on these including methods for nucleic acid enrichment such as by using restriction digestion with polymerase chain reaction and the use of nested primers, may be used in Part B similarly, any method capable of demonstrating amplified nucleic acid product, including but not limited to agarose gel electrophoresis, ELISA detection methods, electrochemiluminescence, high performance liquid chromatography, and reverse dot blot methods, may be used in Part C. In this invention, any of the various methods in Part A may be combined with any method applicable for Part B, which can then be combined with any applicable method in Part C. It is the new application of these methods to the detection of tumor-derived or associated RNA in plasma or serum, and in particular to extracellular RNA but also to plasma or serum intracellular RNA, that makes this invention novel. Several methods applicable for each of Part A, Part B, and Part C, will be described in detail below as a description of the invention. Again, it is to be emphasized that any method in Part A can be combined with any method in Part B with any method in Part C to follow. Furthermore, it should be emphasized that while the contribution of extracellular RNA versus intracellular RNA as detected in plasma or serum may be defined, for example by using filters or high speed centrifugation, it is not a requirement of the invention that such a definition be made.

Either "fresh" blood plasma or serum, or frozen (stored) and subsequently thawed plasma or serum may be used for purposes of this invention. Frozen (stored) plasma or serum should optimally be maintained at storage conditions of −20 to −70 degrees centigrade until thawed and used. "Fresh" plasma or serum should be refrigerated or maintained on ice until used, with RNA extraction being performed as soon as possible.

Blood is drawn by standard methods into a collection tube, preferably siliconized glass, either without anticoagulant for preparation of serum, or with EDTA, sodium citrate, heparin, or similar anticoagulants for preparation of plasma. The preferred method if preparing plasma or serum for storage, although not an absolute requirement, is that plasma or serum be first fractionated from whole blood prior to being frozen. This reduces the burden of extraneous intracellular RNA released from lysis of frozen and thawed cells which might reduce the sensitivity of the amplification assay or interfere with the amplification assay through release of inhibitors to PCR such as porphyrins and hematin. "Fresh" plasma or serum may be fractionated from whole blood by centrifugation, using preferably gentle centrifugation at 300-800×g for five to ten minutes, or fractionated by other standard methods. High centrifugation rates capable of fractionating out apoptotic bodies should be avoided. Since heparin may interfere with RT-PCR, use of heparinized blood may require pretreatment with heparinase as described (23), followed by removal of calcium prior to reverse transcription, as described (23). Thus, EDTA is the preferred anticoagulant for blood specimens in which PCR amplification is planned.

Part A: Extraction of Extracellular RNA from Plasma or Serum

In Part A, RNA extraction methods previously published for the extraction of mammalian intracellular RNA or viral RNA may be adapted, either as published or with modification, for extraction of tumor-derived or associated RNA from plasma and serum. The volume of plasma or serum used in part A may be varied dependent upon clinical intent, but volumes of 100 microliters to one milliliter of plasma or serum are sufficient in part A, with the larger volumes often indicated in settings of minimal or premalignant disease. For example:

Both extracellular RNA and intracellular RNA may be extracted from plasma or serum using silica particles, glass beads, or diatoms, as in the method or adaptations of Boom et al. (24). Application of the method adapted by Cheung et al. (25) is described:

Size fractionated silica particles are prepared by suspending 60 grams of silicon dioxide ($SiO_2$, Sigma Chemical Co., St. Louis, Mo.) in 500 milliliters of demineralized sterile double-distilled water. The suspension is then settled for 24 hours at room temperature. Four-hundred thirty (430) milliliters of supernatant is removed by suction and the particles are resuspended in demineralized, sterile double-distilled water added to equal a volume of 500 milliliters. After an additional 5 hours of settlement, 440 milliliters of the supernatant is removed by suction, and 600 microliters of HCl (32% wt/vol) is added to adjust the suspension to a pH2. The suspension is aliquotted and stored in the dark.

Lysis buffer is prepared by dissolving 120 grams of guinidine thiocyanate (GuSCN, Fluka Chemical, Buchs, Switzerland) into 100 milliliters of 0.1×Tris hydrochloride (Tris-HCl) (pH 6.4), and 22 milliliters of 0.2 M EDTA, adjusted to pH 8.0 with NaOH, and 2.6 grams of Triton X-100 (Packard Instrument Co., Downers Grove, Ill.). The solution is then homogenized.

Washing buffer is prepared by dissolving 120 grams of guinidine thiocyanate (GuSCN) into 100 milliliters of 0.1 M Tris-HCl (pH 6.4).

One hundred microliters to two hundred fifty microliters (with greater amounts required in settings of minimal disease) of plasma or serum are mixed with 40 microliters of silica suspension prepared as above, and with 900 microliters of lysis buffer, prepared as above, using an Eppendorf 5432 mixer over 10 minutes at room temperature. The mixture is then centrifuged at 12,000×g for one minute and the supernatant aspirated and discarded. The silica-RNA pellet is then washed twice with 450 microliters of washing buffer, prepared as above. The pellet is then washed twice with one milliliter of 70% (vol/vol) ethanol. The pellet is then given a final wash with one milliliter of acetone and dried on a heat block at 56 degrees centigrade for ten minutes. The pellet is resuspended in 20 to 50 microliters of diethyl procarbonate-treated water at 56 degrees centigrade for ten minutes to elute the RNA. The sample can alternatively be eluted for ten minutes at 56 degrees centigrade with a TE buffer consisting of 10 millimolar Tris-HCl-one millimolar EDTA (pH 8.0) with an RNase inhibitor (RNAsin, 0.5 U/microliter, Promega), with or without Proteinase X (100 ng/ml) as described by Boom et al. (26). Following elution, the sample is then centrifuged at 12,000×g for three minutes, and the RNA containing supernatant recovered. The RNA extract is now used in Part B.

As an alternative method, both extracellular RNA and intracellular RNA may be extracted from plasma or serum in Part A using the Acid Guanidinium Thiocyanate-Phenol-Chloroform extraction method described by Chomczynski and Sacchi (27) as follows:

The denaturing solution consists of 4 M guanidinium thiocyanate, 25 millimolar sodium citrate, pH 7.0, 0.5% sarcosyl, 0.1 M 2-mercaptoethanol. The denaturing solution is prepared as follows: A stock solution is prepared by dissolving 250 grams of guanidinium thiocyanate (GuSCN, Fluka Chemical) with 293 milliliters of demineralized sterile double-distilled water, 17.6 milliliters of 0.75 M sodium citrate, pH 7.0, and 26.4 milliliters of 10% sarcosyl at 65 degrees centigrade. The denaturing solution is prepared by adding 0.36 milliliters 2-mercaptoethanol/50 milliliters of stock solution.

One hundred microliters to one milliliter of plasma or serum is mixed with one milliliter of denaturing solution. Sequentially, 0.1 milliliter of 2 N sodium acetate, pH 4.0, 1 milliliter of phenol, and 0.2 milliliter of chloroform-isoamyl alcohol (49:1) are added, with mixing after addition of each reagent. The resultant mixture is shaken vigorously for 10 seconds, cooled on ice for 15 minutes, and then centrifuged at 10,000×g for 20 minutes at 4 degrees centigrade. The aqueous phase is then transferred to a clean tube and mixed with 1 milliliter of isopropanol. The mixture is then cooled at −20 degrees centigrade for 1-2 hours to precipitate RNA. After centrifugation at 10,000×g for 20 minutes the resulting RNA pellet is dissolved in 0.3 milliliter of denaturing solution, and then reprecipitated with 1 volume isopropanol at −20 degrees centigrade for one hour. Following another centrifugation at 10,000×g for ten minutes at 4 degrees centigrade, 75 ethanol is added to resuspend the RNA pellet, which is then sedimented and vacuum dried, and then dissolved in 5-25 microliters of 0.5% SDS at 65 degrees centigrade for ten minutes. The RNA extract is now used in Part B.

As the preferred embodiment for Part A, and as an alternative method, extracellular RNA and intracellular RNA may be extracted from plasma or serum in Part A using variations of the acid guanidinium thiocyanate-phenol-chloroform extraction method. For example, in the preferred embodiment RNA is extracted from plasma or serum using TRI reagent, a monophase guanidine-thiocyanate-phenol solution, as described by Chomczyneki (28). One hundred microliters to one milliliter of plasma or serum is processed using one milliliter of TRI Reagent™ (TRI Reagent, Sigma Trisolv™, BioTecx Laboratories, Houston, Tex., TRIzol™, GIBCO BRL/Life Technologies, Gaithersburg, Md., ISOGEN™, Nippon Gene, Toyama, Japan, RNA Stat™ 60, Tel-test, Friendesword, Tex.) according to manufacturer's directions. Minor adaptations may be applied as currently practiced within the art. Thus, from one hundred microliters to one milliliter of plasma or serum is mixed with one milliliter of TRI Reagent. Then 0.2 milliliter of chloroform is mixed for 15 seconds, and the mixture allowed to stand for 3 minutes at room temperature. The mixture is then centrifuged at 4 degrees centigrade for 15 minutes at 12,000×g. The upper aqueous phase is removed to which 0.5 milliliter of isopropanol is mixed, and then left at room temperature for five minutes, followed by centrifugation at 4 degrees centigrade for ten minutes at 12,000×g. The RNA pellet is then washed with one milliliter of 75% ethanol by centrifuging at 12,000×g for 5 minutes. The pellet is air dried and resuspended in 11.2 microliters of RNAse free water. Contamination by polysaccharides and proteoglycans, which may be present in extracellular proteolipid-RNA complexes, may be reduced by modification of the precipitation step of the TRI Reagent™ procedure, as described by Chomczynski and Mackey (29) as follows:

One hundred microliters to one milliliter of plasma or serum is mixed with TRI Reagent™ as per manufacturer's directions, being subjected to phase separation using either chloroform or bromo-chloropropane (30) and centrifugation at 10,000×g for 15 minutes. The aqueous phase is removed and then mixed with 0.25 milliliters of isopropanol followed with 0.25 milliliters of a high-salt precipitation solution (1.2 M NaCl and 0.8 M sodium citrate). The mixture is centrifuged at 10,000×g for 5 minutes and washed with one milliliter of 75% ethanol. The RNA pellet is then vacuum dried and then dissolved in 5-25 microliters of 0.5% SDS at 65 degrees centigrade for ten minutes. The RNA extract is now used in Part B.

Alternative methods may be used to extract RNA from plasma or serum in Part A, including but not limited to centrifugation through a cesium chloride gradient, including the method as described by Chirgwin et al. (31), and co-precipitation of extracellular RNA from plasma or serum with gelatin, such as by adaptations of the method of Fournie et al. (32) to RNA extraction.

Circulating extracellular deoxyribonucleic acid (DNA), including tumor-derived or associated extracellular DNA, is also present in plasma and serum (33). Since this DNA will additionally be extracted to varying degrees during the RNA extraction methods described above, it may be desirable or necessary (depending upon clinical objectives) to further purify the RNA extract and remove trace DNA prior to proceeding to Part B. This may be accomplished using DNase, for example by the method as described by Rashtchian (34), as follows:

For one microgram of RNA, in a 0.5 milliliter centrifuge tube placed on ice, add one microliter of 10×DNase I reaction buffer (200 micromolar Tris-HCl (pH 8.4), 500 micromolar KCl, 25 micromolar $MgCl_2$, one micromolar per milliliter BSA). Add to this one unit DNase I (GIBCO/BRL catalog #18068-015). Then bring the volume to ten microliter with DEPC-treated distilled water, and follow by incubating at room temperature for 15 minutes. The DNase I in then inactivated by the addition of 20 millimolar EDTA to the mixture, and heating for 10 minutes at 65 degrees centigrade. The treated RNA may now go directly to Part B.

Alternatively, primers in Part B may be constructed which favor amplification of the RNA products, but not of contaminating DNA, such as by using primers which span the splice junctions in RNA, or primers which span an intron. Alternative methods of amplifying RNA but not the contaminating DNA include the methods as described by Moore et al. (35), and methods as described by Buchman et al. (36), which employs a du-containing oligonucleotide as an adapter primer.

Part B: Nucleic Acid Application

In Part B, RNA which has been extracted from plasma or serum during Part A, or its corresponding cDNA, is amplified using any nucleic acid amplification assay utilized for detection of low numbers of RNA molecules. Applicable assays include but are not limited to reverse transcriptase polymerase chain reaction (RT-PCR), ligase chain reaction (37), branched DNA signal amplification (38), amplifiable RNA reporters, Q-beta replication, transcription-based amplification, boomerang DNA amplification, strand displacement activation, cycling probe technology, isothermal nucleic acid sequence based amplification (NASBA) (39), and other self-sustained sequence replication assays. It is not necessary to modify these assays from their published methods for Part B. The referenced publications are incorporated herein by reference in their entirety for their descriptions for performing the various assays identified therein. It is the application of these nucleic acid amplification assays to the detection of tumor-derived or associated extracellular RNA in plasma or serum that makes their use novel. The preferred embodiment for Part B uses the reverse transcriptase polymerase chain reaction (RT-PCR).

Primers used in the amplification assay should be based on the specific tumor-derived or associated RNA of interest which characterizes the tumor. Tumor-derived or associated RNA includes but is not limited to:

mRNA related to mutated oncogenes or mutated DNA, a partial list of which includes H-ras, K-ras, N-ras, c-myc, her-2-neu, bcr-abl, fms, src, fos, sis, jun, erb-B-1, VHL, PML/RAR, AML1-ETO, EWS/FLI-1, EWS/ERG mRNA related to tumor suppressor genes, a partial list of which includes p53, RB, MCC, APC, DCC, NF1, WT mRNA related to tumor-associated protein which is found elevated in certain cancers, a partial list of which includes alpha-feto protein (AFP), carcinoembryonic antigen (CEA), TAG-72, CA 19-9, CA-125, prostate specific antigen (PSA), CD44, and hcg (human chorionic gonadotropin)

mRNA related to tumor-derived protein not normally found circulating in blood, a partial list of which includes tyrosinase mRNA, keratin 19 mRNA mRNA related to tumor-specific antigens, such as in MAGE 1, MAGE 2, MAGE 3, MAGE 4, GP-100, and MAGE 6, MUC 18, P97 mRNA or messenger-like RNA associated with ribonucleoproteins and RNA within ribonucleoproteins, a partial list of which includes telomerase RNA, and RNA associated with heterogenous nuclear ribonucleoprotein A1 (hn RNP-A1) and A2/B1 (hn RNP-A2/B1) complexes, and heterogenous nuclear ribonucleoprotein K (hn RNP-K), such as c-myc oncogene RNA, in addition to those RNA previously described above when associated with ribonucleoprotein.

For example, oligonucleotide primer sequences for the bcr-abl transcript may be as follows (40):

Primer 1 at the M-bcr location:

```
                                          (SEQ ID NO: 1)
(5'-TGGAGCTGCAGATGCTGACCAACTCG-3').
```

Primer 2 at the exon II abl location:

```
                                          (SEQ ID NO: 2)
(5'-ATCTCCACTGGCCACAAAATCATACA-3').
```

Primer 3 at the M-bcr location:

```
                                          (SEQ ID NO: 3)
(5'-GAAGTGTTTCAGAAGCTTCTCC-3').
```

Primer 4 at the exon II abl location:

```
                                          (SEQ ID NO: 4)
(5'-TGATTATAGCCTAAGACCCGGA-3').
```

The nested RT-PCR assay yields a 305 or 234 base pair product, depending upon bcr exon 3 expression.

As another example, nested primers for human tyrosinase cDNA amplification can be as follows (41):

```
                                          (SEQ ID NO: 5)
Primer 1 (outer, sense)-
(5'-TTGGCAGATTGTCTGTAGCC-3')

(SEQ ID NO: 6)
Primer 2 (outer, anti-sense)-
(5'-AGGCATTGTGCATGCTGCTT-3')

(SEQ ID NO: 7)
Primer 3 (nested, sense)-
(5-'GTCTTTATGCAATGGAACGC-3')

(SEQ ID NO: 8)
Primer 4 (nested, anti-sense)-
(5'-GCTATCCCAGTAAGTGGACT-3')
```

The outer primers result in a PCR amplification product of 284 base pairs, and the nested primers result in a fragment of 207 base pairs.

The preferred oligonucleotide primer sequences for specific tumor-related or tumor-associated mRNA are previously published, with referenced publications incorporated herein by reference in their entirety.

Some, but not all, amplification assays require reverse transcription of RNA to cDNA. As noted, the method of reverse transcription and amplification may be performed by previously published or re mended procedures, which referenced publications are incorporated herein by reference in their entirety, and modification is not required by the invention beyond steps as described in Part A. Various reverse transcriptases may be used, including, but not limited to, MMLV RT, RNase H mutants of MMLV RT such as SuperScript and SuperScript II (Life Technologies, GIBCO BRL, Gaithersburg, Md.), AMV RT, and thermostable reverse transcriptase from *Thermus Thermophilus*. For example, one method, but not the only method, which may be used to convert RNA extracted from plasma or serum in Part A to cDNA in the protocol adapted from the Superscript II Preamplification system (Life Technologies, GIBCO BRL, Gaithersburg, Md.; catalog no. 18089-011), as described by Rashtchian (34), adapted an follows:

1-5 micrograms of RNA extracted from plasma or serum in Part A in 13 microliters of DEPC-treated water is added to a clean microcentrifuge tube. Then one microliter of either oligo (dT) (0.5 milligram/milliliter) or random hexamer solution (50 ng/microliter) is added and mixed gently. The mixture is then heated to 70 degrees centigrade for 10 minutes and then incubated on ice for one minute. Then, it is centrifuged briefly followed by the addition of 2 microliters of 10× synthesis buffer (200 mM Trio-HCl, pH 8.4, 500 mM KCl, 25 mM magnesium chloride, one milligram/milliliter of BSA), one microliter of 10 m each of dNTP mix, 2 microliters of 0.1 M DTT, one microliter of Superscript II RT (200 U/microliter) (Life Technologies, GIBCO BRL, Gaithersburg, Md.). After gentle mixing, the reaction is collected by brief centrifugation, and incubated at room temperature for ten minutes. The tube is then transferred to a 42 degrees centigrade water bath or heat block and incubated for 50 minutes. The reaction is then terminated by incubating the tube at 70 degrees centigrade for 15 minutes, and then placing it on ice. The reaction is collected by brief centrifugation, and one microliter of RNase H (2 units) is added followed by incubation at 37 degrees centigrade for 20 minutes before proceeding to nucleic acid amplification.

Nucleic acid amplification then proceeds as follows:

To the cDNA mixture add the following: 8 microliters of 10× synthesis buffer (200 mM Tris-HCl, pH 8.4, 500 mM KCl, 25 mM magnesium chloride, 1 mg/ml of BSA), 68 microliters sterile double-distilled water, one microliter amplification primer 1 (10 micromolar), one microliter amplification primer 2 (10 micromolar), one microliter Taq DNA polymerase (2-5 U/microliter). Mix gently and overlay the reaction mixture with mineral oil. The mixture is heated to 94 degrees centigrade for 5 minutes to denature remaining RNA/cDNA hybrids. PCR amplification is then performed in an automated thermal-cycler for 15-50 cycles, at 94 degrees centigrade for one minute, 55 degrees centigrade for 30 to 90 seconds, and 72 degrees centigrade for 2 minutes. The amplified PCR product is then detected in Part C.

Furthermore, if the primers contain appropriate restriction sites, restriction digestion may be performed on the amplified product to allow further discrimination between mutant and wild-type sequences.

Cycling parameters and magnesium concentration may vary depending upon the specific case. For example, an alternative method using nested primers useful for detection of human tyrosinase mRNA in Part B is the method described by Smith et al. (4), as follows:

Primer sequences are as described above for human tyrosinase. Ten microliters of RNA extracted in Part A from plasma or serum are treated for reverse transcription by heating at 90 degrees centigrade for 4 minutes, cooling rapidly, and diluting to 20 microliters with a mixture consisting of 1×PCR buffer (10 ml/liter Tris-HCl, pH 8.4, 50 mmol/liter KCl, 100 microgram/milliliter gelatin), 8 mmol/liter magnesium chloride, 1 mmol/liter each dATP, dCTP, dGTP, and dTTP, 0.25 pmol tyrosinase primer 2 (as previously described), 20 units of 'RNA guard' (Pharmacia), and 4 units of murine moloney leukemia virus reverse transcriptase (Pharmacia). The total mixture is then incubated at 37 degrees centigrade for one hour, half the sample removed, and diluted to 50 microliters containing 1×PCR buffer, 200 micromol/liter each of dATP, dCTP, dGTP, and dTTP, 1.6 mmol/liter magnesium chloride, 150 pmol primer 1 and primer 2, 0.1% Triton X-100, and 1 unit Tag DNA polymerase (Promega). The mixture is overlaid with oil, and heated at 95 degrees centigrade for 5 minutes, followed by 30 cycles of PCR in a thermal cycler at 95 degrees centigrade for 65 seconds, 55 degrees centigrade for 65 seconds, and 72 degrees centigrade for 50 seconds. The products are then reamplified with nested primer 3' and nested primer 4 using 5 microliters in a 1:100 dilution. These were amplified in a 25 microliter reaction volume for an additional 30 cycles. This final amplified PCR product is now detected in Part C, either by being electrophoresed on an agarose gel, or by other method.

The preferred embodiments for Part B amplification of specific tumor-related or tumor-associated RNA, including specific primers, method of reverse transcription, and method of RT-PCR, are described by the following referenced publications which are incorporated herein by reference in their entirety for their description for performing the various assays identified therein.

For Part B amplification of tyrosinase mRNA, a mRNA associated with malignant melanoma, the preferred method Ls that of Brossart et al. (41).

For Part B amplification of Keratin 19 mRNA, a mRNA associated with breast cancer and other epithelial malignancies, the preferred method is that of Datta et al. (5).

For Part B amplification of prostate-specific antigen (PSA) mRNA, a mRNA associated with prostate cancer, the preferred method is that of Katz et al. (72).

For Part B amplification of alpha-fetoprotein (AFP) mRNA, a mRNA associated with hepatocellular carcinoma, testicular cancer, and other cancers, the preferred method is that of Komeda et al. (54).

For Part B amplification of BCR/abl mRNA, a mRNA associated with chronic myeloid leukemia (CML), the preferred method is that of Stock et al. (57), or alternatively, by the method of Edmonds et al. (40).

For Part B amplification of carcinoembryonic antigen (CEA) mW, a mRNA associated with gastrointestinal cancers and breast cancer, the preferred method is that of Gerhard et al. (58).

For Part B amplification of P97 mRNA, a mRNA associated with malignant melanoma, the preferred method is that of Hoon et al. (59).

For Part B amplification of MUC 18 mRNA, a mRNA associated with malignant melanoma, the preferred method is that of Hoon et al. (59).

For Part B amplification of PML/RAR-α mRNA, a mRNA associated with acute promyelocytic leukemia, the preferred method is that of Miller et al. (60).

For Part B amplification of CD44 mRNA, a mRNA associated with lung cancer, the preferred method is that of Penno et al. (61).

For Part B amplification of EWS/FLI-1 mRNA, a mRNA associated with Ewing's sarcoma and other Ewing's tumors, the preferred method is that of Pfleiderer et al. (62).

For Part B amplification of EWS/ERG mRNA, a mRNA associated with Ewing sarcoma and other Ewing's tumors, the preferred method is that of Pfleiderer et al. (62).

For Part B amplification of AML1/ETO mRNA, a mRNA associated with acute myelogenous leukemia, the preferred method is that of Maruyama at al. (63).

For Part B amplification of MAGE mRNA, including mRNA of MAGE-1, MAGE-2, MAGE-3, and MAGE-4, which are associated with bladder cancer, ovarian cancer, melanoma, lung cancer, head and neck cancer, and others, the preferred method is that of Patard et al. (64).

For Part B amplification of beta-human chorionic gonadotropin mRNA, a mRNA associated with malignant melanoma, germ cell tumors and other cancers, the preferred method is that of Doi et al. (65).

For Part B amplification of human Telomerase-associated RNA, the preferred method is by application of the TRAP PCR method as described by Kim et al (69). Alternatively, other amplification methods may be used as described herein where primer selection is designed based upon the human Telomerase template sequence as described by Feng et al (76).

Alternative methods of nucleic acid amplification which may be used in Part B include other variations of RT-PCR, including quantitative RT-PCR, for example as adapted to the method described by Wang et al. (43) or by Karet et al. (44).

An alternative method of nucleic acid amplification which may be used in Part B is ligase chain reaction (66). Extracellular RNA extracted from plasma or serum in Part A must be reverse transcribed to cDNA. Oligonucleotide primers are selected which lie directly upon the cDNA site of interest. If a mutation site is present, oligonucleotides which are complementary to the site are made to contain the mutation only at their 3-prime end, excluding hybridization of non-mutated, wild-type DNA. Restriction sites can also be utilized to discriminate between mutant and wild-type sequences if necessary.

An alternative method of either qualitative or quantitative amplification of nucleic acid which may be used in Part B is branched DNA signal amplification, for example as adapted to the method described by Urdea et al. (38), with modification from the reference as follows: plasma or serum should only be centrifuged at lower speeds, an previously outlined. Extracellular RNA is then extracted from plasma or serum an described in Part A, and then added directly to microwells. The method for detection of tumor-related or tumor-associated RNA then proceeds as referenced (38), with target probes specific for the tumor-related or tumor-associated RNA or cDNA of interest, and with chemiluminescent light emission proportional to the amount of tumor-associated RNA in the plasma or serum specimen. The specifics of the referenced method are described further by Urdea et al (71) with this reference incorporated herein in its entirety.

An alternative method of either qualitative or quantitative amplification of nucleic acid which may be used in Part B is isothermal nucleic acid sequence based amplification (NASBA), for example as adapted to the method described by Kievits et al. (39), or by Vandamme et al. (45). The method of Sooknanan et al. (67) may be used for the detection and quantification of BCR/ABL mRNA.

Alternative methods of either qualitative or quantitative amplification of nucleic acids which may be used in Part B include, but are not limited to, Q-beta replication, other self-sustained sequence replication assays, transcription-based amplification assays, and amplifiable RNA reporters, boomerang DNA amplification, strand displacement activation, and cycling probe technology.

The amplified product from Part B is next detected in Part C. Depending upon the detection method used in Part C, primers may need to be biotinylated or otherwise modified in Part B.

Part C: Detection of Amplified Product

There are numerous methods to detect amplified nucleic acid product, any of which may be used in Part C to detect the amplified product from Part B. The referenced publications, including those pertaining to detection of specific tumor-related or associated RNA or its corresponding cDNA as previously cited, and those pertaining to RNA or its corresponding cDNA detection as follows, are incorporated herein by reference in, their entirety for the descriptions for performing the various assays identified therein.

In the preferred method, amplified product is detected in Part C using gel electrophoresis. In the preferred embodiment, 25 microliters of amplified (or post-amplification digested) product is electrophoresed through a 3% agarose gel in 1×TBE at 75 VDC. Electrophoresis is carried out for one to two hours before staining with ethidium bromide. As an alternative to ethidium bromide, the amplified product can be transferred from the gel to a membrane by blotting techniques to be detected with a labeled probe (46).

An alternative method which may be used in Part C to detect the amplified product from Part B is ELISA detection. Depending upon the ELISA detection method used, it may be necessary to biotinylate or otherwise modify the primers used in part B.

For example, one ELISA detection method which may be used in Part C is the method described by Landgraf et al. (47), as follows:

Primers are modified with biotinylamidocaproat-N-hydroxysuccinimidester (Sigma) and fluoroescein isothiocyanate (FITC) (Sigma) by the method of Landgraf et al. (48). Following invention Part B, the ELISA is carried out in microtiter plates coated with 1 microgram/milliliter affinity-purified avidin (13 U/mg, Sigma). One microliter of the final amplification product (or post-digestion product) is diluted with 50 microliters of PBS-Tween, and then incubated at room temperature for 30 minutes in the microtiter plate well. Non-incorporated primers are removed by washing with PBS-Tween. The plates are then incubated at room temperature for 30 minutes after adding 50 microliters per well of anti-FITC antibody-HRPO conjugate (Dakopatts) which in at a 1:500 dilution with PBS-Tween. Following this, 80 microliters of an ELISA solution made from one milligram 3,3',5,5'-tetramethylbenzidin (Sigma) dissolved in one milliliter dimethyl sulfoxide, and diluted 1:10 with 50 millimol Na-acetate:citric acid, pH 4.9, with 3 microliter of 30% (vol/vol) Hz % added, is added to each well. After 2-5 minutes, the reaction is stopped by adding 80 microliter of 2H $H_2SO_4$. The optical density is then read at 450 nm.

Alternative methods of ELISA detection which may be used in Part C include, but are not limited to, immunological detection methods using monoclonal antibody specific for RNA/DNA hybrids, such as by adapting methods described by Coutlee et al. (49), or by Bobo et al. (50), which publications are also incorporated herein by reference in their entirety for their description of the detection methods identified therein.

Alternative methods of ELISA detection which may be used in Part C include, but are not limited to, commercial detection systems such as the SHARP signal system (Digene Diagnostics, Inc.), and the DNA enzyme immunoassay (DEIA), (GEN-ETI-K DEIA, Sorin Biomedica).

Alternative methods by which amplified product from Part B may be detected in Part C include but are not limited to all methods of electrochemiluminescence detection, such as by adapting the method described by Blackburn et al. (51), or by DiCesare et al. (52), and all methods utilizing reverse dot blot detection technology (S3), and all methods utilizing high-performance liquid chromatography.

Therapeutic Applications

The extraction of extracellular tumor-associated or derived RNA from plasma or serum, and the amplification of that RNA or its corresponding cDNA to detectable levels, permits further analysis or other manipulation of that RNA, or the corresponding cDNA, from which further clinical utility is realized. In this optional step of the invention, amplified extracellular RNA or the corresponding cDNA is analyzed to define the characteristics or composition of the tumor from which the RNA originates. Any of several methods may be used, dependent upon the desired information, including nucleic acid sequencing, spectroscopy including proton NMR spectroscopy, biochemical analysis, and immunologic analysis. In the preferred embodiment, amplified cDNA is isolated—for example by excising DNA bands from an agarose gel—reamplified, cloned into a plasmid vector, for example the pGEM-T vector plasmid (Promega) and sequenced using a commercial kit such as Sequenase 2.0 (USB). Analysis to define the characteristics or composition of the tumor-associated RNA in plasma or serum, and thus the tumor of origin, affords a wide array of clinical utility, including the description, characterization, or classification of the tumor, whether known or occult, such as by tissue of origin, by type (such as premalignant or malignant), phenotype, and genotype, and by description or characterization of tumor behavior, physiology and biochemistry, as to gain understanding of tumor invasiveness, propensity to metastasize, and sensitivity or resistance to various therapies, thereby allowing the prediction of response to either ongoing or planned therapy and, further, allowing evaluation of prognosis. Comparison of the characteristics of extracellular RNA to previous biopsy or surgical specimens permits further evaluation of tumor heterogeneity or similarity in comparison to that specimen, and thus evaluation of tumor recurrence.

Following extraction of extracellular tumor-derived or tumor-associated RNA from plasma or serum and amplification of the corresponding cDNA, ribonucleic acid (RNA) may be transcribed or manufactured back from the amplified DNA as a further option. Transcription of RNA may be performed by employing a primer with an RNA polymerase promoter region joined to the standard primer sequence of the cDNA in an amplification reaction. RNA is then transcribed from the attached promoter region. In the preferred embodiment, amplified cDNA is cloned into an expression vector, and RNA is transcribed. Furthermore, as an optional preferred embodiment, the RNA is used in an in vitro translation reaction to manufacture tumor-associated or tumor-specific protein or associated peptides or oligopeptides, according to methods currently known in the art (73-76). Note, these cited references, and those to follow, are incorporated herein by reference in their entirety for their description for performing the various assays identified therein.

Extraction of tumor-derived or tumor-associated extracellular RNA, its amplification, characterization, and translation to tumor-associated or tumor-specific protein, provides significant utility, both in the assignment of therapy and in the development of tumor-specific therapies sequencing of RNA or cDNA allows assignment or development of antisense compounds, including synthetic oligonucleotides and other antisense constructs appropriately specific to the DNA, such as by construction of an expression plasmid such as by adapting the method of Aoki et al. (68) which is incorporated by reference in its entirety, or by other construction and use as referenced (77-81). Thus, application of the invention in this manner would entail the extraction of tumor-associated RNA from plasma or serum, followed by an optional step of reverse transcribing to cDNA, followed by amplification of the RNA or cDNA. The amplified product can then be sequenced to define the nucleic acid sequence of the tumor-associated RNA or cDNA. An antisense oligonucleotide is then constructed in much, a manner as referenced above specific to the defined sequence, or alternatively, an already manufactured antisense compound is determined to be applicable, or may be manufactured when the sequence is known based upon knowledge of the primer sequence. Similarly, defining tumor characteristics by analysis of extracellular RNA allows assignment of specific monoclonal antibody or vaccine therapies appropriately specific to the tumor. Production of corresponding immunologic protein can be used in the development of tumor-specific monoclonal antibodies. Thus, application of the invention in this manner would entail the extraction of tumor-associated RNA from plasma or serum, followed by amplification to obtain a tumor-associated amplified product. The amplified product is translated, or transcribed and translated, into a protein or associated peptides or oligopeptides as previously described, thus providing a tumor-associated antigen. The tumor-associated antigen thus enables production of a monoclonal antibody directed against the antigen by use of hybridoma technology or other methods as currently practiced by the art (82). Said monoclonal antibody may further be conjugated with a toxin or other therapeutic agent (83), or with a radionucleotide (84) to provide further therapeutic or diagnostic use directed against the tumor. Similarly, translated protein or associated peptides or oligopeptides can be used in tumor-specific vaccine development. Furthermore, the extracellular R and complimentary DNA permit a means of defining or allowing the construction of a DNA construct which may be used in vaccine therapy.

Specifically, the invention is applied to either define or obtain tumor-associated protein or peptides, RNA, or cDNA, by methods as previously described, and from which a tumor-directed vaccine may be developed or constructed. The methods by which the vaccine is further developed or constructed vary, but are known to the art (85-90), and are referenced herein in their entirety.

Of particular value, the invention allows the development and application of these tumor-specific therapies even when only premalignant tumors, early cancers, or occult cancers are present. Thus, the invention allows therapeutic intervention when tumor burden is low, immunologic function is relatively intact, and the patient is not compromised, all increasing the potential for cure.

Hypothetical Examples of the Invention

In the following examples, illustrative hypothetical clinical cases are presented to demonstrate the potential clinical use of the invention.

Case 1

A 26 year old asymptomatic hypothetical man presents for evaluation after learning his 37 year old brother was recently diagnosed with colon cancer. Peripheral blood is drawn in order to use the invention to evaluate for the presence of extracellular CEA mRNA in the patient's plasma. Plasma extracellular RNA is extracted during invention Part A by the Acid Guanidinium thiocyanate-Phenol-chloroform extraction method as previously described, followed by qualitative RT-PCR amplification in invention Part B using CEA mRNA primers as previously described. The amplification assay as previously described (58) is performed in invention Part B. The final amplified product is detected by gel electrophoresis on a 3% agarose gel in invention Part C. Results are positive in this patient indicating the presence of CEA mRNA in the blood plasma.

CEA has been associated with colon cancer. While colon cancer is highly curable if diagnosed at an early stage, it is fatal when diagnosed at advanced metastatic stages. The positive results of the invention for this patient, in the setting of a strongly positive family history for colon cancer, are suggestive of either premalignant or malignant colon cancer. It is recommended that the patient undergo colonoscopy, and if no lesion is found, receive surveillance more frequently than would normally be given.

This hypothetical case illustrates how the invention can be used to screen high risk patients for cancer, detect either premalignant or malignant conditions prior to the metastatic state, and play a role in clinical management. While CEA mRNA is associated with other cancers, such as liver cancer, the addition of a multiplex panel approach using the invention to detect multiple different tumor-associated extracellular RNA, including for example K-ran, P53, DCC, and APC RNA, enables clarification as to whether the CEA mRNA is likely associated with a colon tumor, and further, whether the findings are consistent with a premalignant or a malignant tumor.

Case 2

A 33 year old hypothetical woman sees her local dermatologist after noting a "bleeding mole" on her back. Local excision diagnoses a malignant melanoma of 0.3 millimeter depth. Wide surgical re-excision is performed, and the patient is told she is likely cured and no further therapy is needed. Three months following her surgery the patient seeks a second opinion regarding the need for further therapy. Peripheral blood is drawn to evaluate her plasma for the presence of extracellular tyrosinase messenger RNA by the invention.

Plasma extracellular RNA is extracted in invention Part A using the preferred TRI-Reagent method as previously described, followed by RT-PCR using nested primers for tyrosinase cDNA in invention Part B as previously described, with ELISA detection in invention Part C. Invention results detect the presence of tyrosinase mRNA in the patient's plasma. Tyrosinase is common to both normal melanocytes and malignant melanoma. However, tyrosinase mRNA does not normally circulate in blood, and its presence in plasma indicates latent malignant melanoma. Consequently, the patient is started on adjuvant therapy with interferon-alpha. Plasma extracellular tyrosinase RNA levels are subsequently serially followed in a quantitative fashion using the invention. Blood is drawn from the patient every two months, and plasma extracellular RNA is extracted in invention Part A using the silica extraction method as previously described. Quantitative RT-PCR amplification for tyrosinase mRNA is then performed in invention Part B using biotinylated primer using electrochemiluminescence based detection in invention Part C. Invention data demonstrates a serial rise in the patient's plasma extracellular tyrosinase mRNA levels. Consequent to this data, the interferon is stopped, and the patient is enrolled into an experimental adjuvant therapy protocol.

This hypothetical case illustrates several uses of the invention, including the detection of latent cancer, predicting prognosis and cancer recurrence following surgical excision, determining the need for additional therapy, evaluating the benefit of therapy and the need to change therapies, and evaluating prognosis of patients on therapy.

Case 3

A 76 year old hypothetical man is noted to have a pancreatic mass on CT scan Imaging. His chest x-ray and colonoscopy are normal. The patient refuses to consider surgery because of the significant surgical risks. He elects to receive patient-specific therapy made possible by use of the invention. Since K-ras mutations are present in 80-90% of pancreatic cancers, peripheral blood is drawn to evaluate for and characterize extracellular mutant K-ran RNA circulating in plasma using the invention. Plasma extracellular RNA is extracted in invention Part A using the TRI reagent extraction method as previously described, followed by RT-PCR in invention Part B, with high performance liquid chromatography detection in Part C. Mutant K-ras amplification products are then separated following chromatography and the K-ras mutation is sequenced using standard techniques as previously described. Detection of mutant K-ras mRNA in the plasma confirms the likelihood of the pancreatic mass being a pancreatic cancer. Based upon the mutation sequence, a patient-specific therapy (i.e., specific to the patient's own cancer) is developed, in this case a ras vaccine specific to the mutant oncogene in this patient's pancreatic cancer. Alternatively, mutant X-ras specific protein, generated as previously described, may be used to develop a tumor-specific monoclonal antibody.

In this hypothetical case, the invention is used not only to help confirm a suspected diagnosis of pancreatic cancer, but to develop a patient-specific therapy. Patient-specific therapies—i.e., therapies specifically designed for a given patient's cancer, or a given type of cancer, are possible when specific characteristics of the tumor are recognized. Since the invention results in amplification of pure tumor product, it becomes possible to characterize the tumor, in this case using sequence analysis and/or transcription and translation. The technological leap that the invention enables is that it allows tumors to be characterized without the need for biopsy or surgery. Thus, it becomes possible to treat tumors even before they become clinically evident, i.e., treating at latent stages, pre-recurrence stages, or even pre-malignant stages. Early treatment of cancer before metastatic cells enter the bloodstream increases the likelihood of cure.

Case 4

A 36 year old hypothetical woman who has three small children at home was diagnosed with breast cancer two years ago. She had been treated with surgery followed by six months of chemotherapy. In addition, her blood serum has been serially evaluated for extracellular keratin 19 mRNA using the invention in which serum extracellular kerain 19 mRNA is extracted in invention Part A using the silica extraction method, followed by RT-PCR amplification in invention Part B with ELISA detection in invention Part C. Keratin 19 mRNA encodes for an intermediate filament protein not normally found in blood which can serve as a marker for breast cancer. While previous results for this patient had been negative, her blood serum is now testing positive for extracellular keratin 19 mRNA by the invention, suggesting an impending cancer recurrence. A multiplex panel for serum extracellular myc, ras, P53, EGFr, and Her-2-neu RNA is performed using the invention. This data confirms that tumor characteristics are identical to those of the original breast cancer primary, confirming a recurrence rather than a new primary. Consequently, serum extracellular keratin 19 mRNA is measured in a quantitative fashion using a branched DNA signal amplification assay in invention Part B, with measurements performed 2 months and 4 months later. Quantitative measurements indicate increasing levels of keratin 19 mRNA, and allow extrapolation to predict that clinical recurrence will be noted in approximately 2 years. This information allows both the physician and the patient to plan future therapeutic options in the context of the patient's current social and family situation.

This hypothetical case illustrates the use of the invention to monitor patients following therapy for recurrence of their cancer, to determine characteristics of their tumor, and to predict prognosis. Breast cancer patients have a high incidence of second primaries, but the invention permits delineation of primary versus recurrent cancer by using a multiplex panel approach to evaluate tumor characteristics. Furthermore, since quantitative analysis in invention Part B allows clarification of prognosis, the patient is in a better position to plan therapy within the context of her social/family situation. Lastly, since the invention allows detection of tumor-derived extracellular RNA, and does not depend upon the presence of circulating cancer cells, recurrence can be detected at a very early stage (in this hypothetical case—2 years before clinical detection), which increases the likelihood of effective therapy.

I claim:
1. A method for detecting a ribonuclease-resistant extracellular human RNA in blood plasma or serum from a human, wherein the ribonuclease-resistant extracellular human RNA is tyrosinase RNA, keratin 19 RNA, prostate-specific antigen RNA, breakpoint cluster region/c-abl oncogene 1 fusion gene (BCR/abl) RNA, carcinoembryonic antigen RNA, p97 RNA, melanoma cell adhesion molecule (MUC 18) RNA, promyelocytic leukemia-retinoic acid receptor alpha gene fusion gene (PML/RAR) RNA, CD44 RNA, Ewing's sarcoma breakpoint region 1-Friend leukemia virus integration fusion gene (EWS/FLI-1) RNA, Ewing's sarcoma breakpoint region 1-v-ets erythroblastosis virus E26 oncogene like fusion gene (EWS/ERG) RNA, acute myelogenous leukemia 1-ETO fusion gene (AML 1/ETO) RNA, beta human chorionic gonadotropin RNA, telomerase RNA, von Hippel-Lindau tumor suppressor (VHL) RNA, mutated in colorectal cancers (MCC) RNA, adenomatous polyposis coli (APC) RNA, deleted in colorectal carcinoma (DCC) RNA, neurofibromin 1 (NF1) RNA, Wilm's tumor gene (WT) RNA, tumor associated glycoprotein-72 (TAG-72) RNA, carbohydrate antigen 19-9 (CA 19-9) RNA, carcinoma antigen-125 (CA-125) RNA, melanoma antigen family A-1 (MAGE 1) RNA, melanoma antigen family A-2 (MAGE 2) RNA, melanoma antigen family A-3 (MAGE 3) RNA, melanoma antigen family A-4 (MAGE 4) RNA, melanoma antigen family A-6 (MAGE 6) RNA, melanosomal matrix protein 17 (GP-100) RNA, heterogeneous nuclear ribonucleoprotein-A1 (hn RNP-A1) RNA, heterogeneous nuclear ribonucleoprotein-A2/B1 (hn RNP-A2/B1) RNA, or heterogeneous nuclear ribonucleoprotein-K (hn RNP-K) RNA, the method comprising the steps of:
   a) isolating blood plasma or serum from a whole blood specimen of a human, wherein said whole blood specimen contains an active plasma ribonuclease, and wherein said blood plasma or serum contains ribonuclease-resistant extracellular human RNAs complexed to lipid or proteolipid or ribonuclease-resistant extracellular human RNAs that are protein-bound or within an apoptotic body;
   b) extracting extracellular human RNA from said blood plasma or serum, wherein said extracellular human RNA comprises a ribonuclease-resistant extracellular human RNA present in said blood plasma or serum that is tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A1 RNA, hn RNP-A2/B1 RNA, or hn RNP-K RNA;
   c) producing an amplified product from said extracellular human RNA or cDNA produced therefrom by amplification, wherein said amplification is performed either qualitatively or quantitatively using primers or probes specific for the ribonuclease-resistant extracellular human RNA that is tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A1 RNA, hn RNP-A2/B1 RNA, or hn RNP-K RNA, or cDNA thereof; and
   d) detecting the amplified product, wherein the detection of the amplified product indicates the presence of said ribonuclease-resistant extracellular human RNA in the blood plasma or serum of the human and said ribonuclease-resistant extracellular human RNA is tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A 1 RNA, hn RNP-A2/B1 RNA, or hn RNP-K RNA.

2. The method of claim 1, wherein the amplification is performed using a method that is: a) polymerase chain reaction or reverse transcriptase polymerase chain reaction; b) amplification using RNA reporters; c) Q-beta replication; d) transcription-based amplification; e) isothermal nucleic acid sequence replication assay; f) boomerang DNA amplification; or g) a combination or variation thereof.

3. The method of claim 1, wherein said detecting the amplified product is performed using a method that is: a) an electrophoresis-based detection method; b) an enzyme linked immunosorbant assay (ELISA) detection method; c) an immunological detection method using monoclonal antibodies; d) a detection method using a labeled fluorescent or chromagenic probe; e) Southern blot analysis; f) an electrochemiluminescence-based detection method; g) reverse dot blot detection; or h) a high performance liquid chromatography-based detection method.

4. The method according to claim 1, wherein the amplified product is further characterized by: a) nucleic acid sequencing; b) spectroscopy c) immunological analysis; and d) production of the corresponding protein of said ribonuclease-resistant extracellular human RNA.

5. A method for detecting a ribonuclease-resistant extracellular human RNA species in blood plasma or serum from a human, wherein said ribonuclease-resistant extracellular human RNA species is tyrosinase RNA, keratin 19 RNA, prostate-specific antigen RNA, breakpoint cluster region/c-abl oncogene 1 fusion gene (BCR/abl) RNA, carcinoembryonic antigen RNA, p97 RNA, melanoma cell adhesion molecule (MUC 18) RNA, promyelocytic leukemia-retinoic acid receptor alpha gene fusion gene (PML/RAR) RNA, CD44 RNA, Ewing's sarcoma breakpoint region 1-Friend leukemia virus integration fusion gene (EWS/FLI-1) RNA, Ewing's sarcoma breakpoint region 1-v-ets erythrobastosis virus E26 oncogene like fusion gene (EWS/ERG) RNA, acute myelogenous leukemia 1-ETO fusion gene (AML1/ETO) RNA, beta human chorionic gonadotropin RNA, telomerase RNA, Von Hippel-Lindau tumor suppressor (VHL) RNA, mutated in colorectal cancers (MCC) RNA, adenomatous polyposis coli (APC) RNA, deleted in colorectal cancer (DCC) RNA, neurofibromin 1 (NF1) RNA, Wilm's tumor gene (WT) RNA, tumor associated glycoprotein-72 (TAG-72 RNA), carbohydrate antigen 19-9 (CA 19-9) RNA, carcinoma antigen-125 (CA-125) RNA, melanoma antigen family A-1 (MAGE 1) RNA, melanoma antigen family A-2 (MAGE 2) RNA, melanoma antigen family A-3 (MAGE 3) RNA, melanoma antigen family A-4 (MAGE 4) RNA, melanoma antigen family A-6

(MAGE 6) RNA, melanosomal matrix protein 17 (GP-100) RNA, heterogeneous nuclear ribonucleoprotein-A1 (hn RNP-A1) RNA, heterogeneous nuclear ribonucleoprotein-A2/B1 (hn RNP-A2/B1) RNA, or heterogeneous nuclear ribonucleoprotein-K (hn RNP-K) RNA, the method comprising the steps of obtaining blood plasma or serum from a whole blood specimen of a human, wherein said whole blood specimen contains an active plasma ribonuclease, extracting human RNA from said blood plasma or serum from the human, wherein said human RNA comprises a ribonuclease-resistant extracellular human RNA species present in said blood plasma or serum, and hybridizing said ribonuclease-resistant extracellular human RNA species or cDNA thereof, to a nucleic acid probe specific for said ribonuclease-resistant extracellular human RNA species, wherein said ribonuclease-resistant extracellular human RNA species is tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A1 RNA, hn RNP-A2/B1 RNA, or hn RNP-K RNA, thereby detecting a hybridization between said probe and said ribonuclease-resistant extracellular human RNA species indicates the presence of said ribonuclease-resistant extracellular human RNA species in the blood plasma or serum of the human.

6. The method of claim 5, wherein the human is a human with cancer.

7. A method of detecting at least two RNA species of a plurality of ribonuclease-resistant extracellular human RNA species in blood plasma or serum from a human, wherein at least one RNA species of the at least two RNA species of the plurality of ribonuclease-resistant extracellular human RNA species present in the blood plasma or serum is tyrosinase RNA, keratin 19 RNA, prostate-specific antigen RNA, breakpoint cluster region/c-abl oncogene 1 fusion gene (BCR/abl) RNA, carcinoembryonic antigen RNA, p97 RNA, melanoma cell adhesion molecule (MUC 18) RNA, promyelocytic leukemia-retinoic acid receptor alpha gene fusion gene (PML/RAR) RNA, CD44 RNA, Ewing's sarcoma breakpoint region 1-Friend leukemia virus integration fusion gene (EWS/FLI-1) RNA, Ewing's sarcoma breakpoint region 1-v-ets erythroblastosis virus E26 oncogene like fusion gene (EWS/ERG) RNA, acute myelogenous leukemia 1-ETO fusion gene (AML1/ETO) RNA, beta human chorionic gonadotropin RNA, telomerase RNA, von Hippel-Lindau tumor suppressor (VHL) RNA, mutated in colorectal cancers (MCC) RNA, adenomatous polyposis coli (APC) RNA, deleted in colorectal carcinoma (DCC) RNA, neurofibromin 1 (NF 1) RNA, Wilm's tumor gene (WT) RNA, tumor associated glycoprotein-72 (TAG-72) RNA, carbohydrate antigen 19-9 (CA 19-9) RNA, carcinoma antigen-125 (CA-125) RNA, melanoma antigen family A-1 (MAGE 1) RNA, melanoma antigen family A-2 (MAGE 2) RNA, melanoma antigen family A-3 (MAGE 3) RNA, melanoma antigen family A-4 (MAGE 4) RNA, melanoma antigen family A-6 (MAGE 6) RNA, melanosomal matrix protein 17 (GP-100) RNA, heterogeneous nuclear ribonucleoprotein-A1 (hn RNP-A1) RNA, heterogeneous nuclear ribonucleoprotein-A2/B1 (hn RNP-A2/B1) RNA, or heterogeneous nuclear ribonucleoprotein-K (hn RNP-K) RNA, the method comprising the steps of:

a) isolating blood plasma or serum from a whole blood specimen of a human, wherein said whole blood specimen contains an active plasma ribonuclease;

b) extracting extracellular human RNA from said blood plasma or serum from the human, wherein said extracellular human RNA comprises a plurality of ribonuclease-resistant extracellular human RNA species present in said blood plasma or serum and wherein the at least one RNA species of the at least two RNA species of the plurality of ribonuclease-resistant extracellular human RNA species present in said blood plasma or serum is tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A1 RNA, hn RNP-A2/B1 RNA, or hn RNP-K RNA;

c) amplifying concurrently or sequentially the at least two RNA species of said plurality of ribonuclease-resistant extracellular human RNA or cDNA produced therefrom using primers specific for the at least two RNA species of said plurality of ribonuclease-resistant extracellular human RNA or cDNA produced therefrom, wherein the at least one RNA species of the at least two RNA species of the plurality of ribonuclease-resistant extracellular human RNA species is tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A1 RNA, hn RNP-A2/B1 RNA, or hn RNP-K RNA, and producing at least two different amplified products; and d) detecting the at least two different amplified products, thereby detecting said at least two RNA species of said plurality of ribonuclease-resistant extracellular human RNA species in the blood plasma or serum from the human, wherein detecting at least one of the at least two different amplified products produced from the amplification of tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A1 RNA, hn RNP-A2/B1 RNA, or hn RNP-K RNA, or cDNA therefrom indicates the presence of tyrosinase RNA, keratin 19 RNA, prostate-specific antigen RNA, BCR/abl RNA, carcinoembryonic antigen RNA, p97 RNA, MUC 18 RNA, PML/RAR RNA, CD44 RNA, EWS/FLI-1 RNA, EWS/ERG RNA, AML1/ETO RNA, beta human chorionic gonadotropin RNA, telomerase RNA, VHL RNA, MCC RNA, APC RNA, DCC RNA, NF1 RNA, WT RNA, TAG-72 RNA, CA 19-9 RNA, CA-125 RNA, MAGE 1 RNA, MAGE 2 RNA, MAGE 3 RNA, MAGE 4 RNA, MAGE 6 RNA, GP-100 RNA, hn RNP-A 1 RNA, hn RNP-A2/B1 RNA, or hn RNP-K RNA in the blood plasma or serum of the human.

* * * * *